(12) United States Patent
Napoletano et al.

(10) Patent No.: US 7,488,811 B2
(45) Date of Patent: Feb. 10, 2009

(54) MACROLIDE COMPOUNDS ENDOWED WITH ANTIINFLAMMATORY ACTIVITY

(75) Inventors: Mauro Napoletano, Milan (IT); Ermanno Moriggi, Busto Arsizio (IT); Andrea Mereu, Como (IT); Fernando Ornaghi, Carlazzo (IT); Gabriele Morazzoni, Lainate (IT); Roberto Longoni, Locate Varesino (IT); Carlo Riva, Inverigo (IT); Luciano Pacchetti, Locate Varesino (IT); Franco Pellacini, Milan (IT)

(73) Assignee: Zambon Group S.p.A., Bresso (IT)

( * ) Notice: Subject to any disclaimer, the term of this patent is extended or adjusted under 35 U.S.C. 154(b) by 98 days.

(21) Appl. No.: 10/522,671

(22) PCT Filed: Jul. 29, 2003

(86) PCT No.: PCT/EP03/08448

§ 371 (c)(1),
(2), (4) Date: Aug. 4, 2005

(87) PCT Pub. No.: WO2004/013153

PCT Pub. Date: Feb. 12, 2004

(65) Prior Publication Data

US 2006/0058246 A1    Mar. 16, 2006

(30) Foreign Application Priority Data

Aug. 1, 2002    (IT)    .......................... MI2002A1726

(51) Int. Cl.
*A61K 31/70*    (2006.01)
(52) U.S. Cl. ......................................... 536/7.4; 536/7.2
(58) Field of Classification Search .................. 536/7.2, 536/7.3, 7.4; 514/29
See application file for complete search history.

(56) References Cited

U.S. PATENT DOCUMENTS

| | | | |
|---|---|---|---|
| 3,478,014 A | 11/1969 | Djokic et al. | |
| 3,725,385 A | 4/1973 | Freiberg | |
| 3,923,784 A | 12/1975 | Kierstead et al. | |
| 3,928,387 A | 12/1975 | Kierstead et al. | |
| 4,743,593 A | 5/1988 | Hunt | |
| 5,892,008 A * | 4/1999 | Ku et al. ..................... | 536/18.5 |
| 5,969,161 A * | 10/1999 | Bonnet et al. ................ | 549/271 |
| 6,043,226 A * | 3/2000 | Lundy et al. .................. | 514/29 |
| 6,096,714 A * | 8/2000 | Agouridas et al. ............. | 514/29 |

FOREIGN PATENT DOCUMENTS

| | | |
|---|---|---|
| EP | 0 254 534 | 1/1988 |
| EP | 0 682 038 | 11/1995 |
| EP | 0 771 564 | 5/1997 |
| EP | 0 775 489 | 5/1997 |
| EP | 0 941 998 | 9/1999 |
| FR | 2 735 694 | 12/1996 |
| JP | 2001 181294 | 7/2001 |
| WO | 92/16226 | 10/1992 |
| WO | 96/18633 | 6/1996 |
| WO | 97/00684 | 1/1997 |
| WO | 99/16779 | 4/1999 |
| WO | 00 42055 | 7/2000 |

OTHER PUBLICATIONS

Takizawa, Hajime et al. "Erythromycin Modulates IL-8 Expression in Normal and Inflamed Human Bronchial Epithelial Cells", Am. J. Respir. Crit. Care Med., vol. 156, pp. 266-271.

Tamaoki, Jun et al. "Macrolide Antibiotics Protect against Endotoxin-Induced Vascular Leakage and Neutrophil Accumulation in Rat Trachea", Antimicrobial Agents and Chemotherapy, vol. 38, No. 7, pp. 1641-1643 1994.

Suzuki, Tomoko et al. "Erythromycin and Common Cold in COPD", Chest, vol. 120, pp. 730-733 2001.

Labro, Marie Therese. "Immunomodulatory Actions of Antibacterial Agents", Clin. Immunother., vol. 6, pp. 454-464 1996.

Faghih, Ramin et al., "Synthesis and Antibacterial Activity of (9S)-9-Dihydroclarithromycin", Journal of Antibiotics, vol. 43, pp. 1334-1336 1990.

Anderson, Ronald et al. "Membrane-Stabilizing, Anti-Inflammatory Interactions of Macrolides with Human Neutrophils", Inflammation, vol. 20, No. 6, pp. 693-705 1996.

Stvrtinova, Viera et al. "Inflammation and Fever", Academic Electronic Press 1995.

Woodward, R.B. et al. "Asymmetric Total Synthesis of Erythromycin. 2. Synthesis of an Erythronolide A Lactone System", J. Am. Chem. Soc., vol. 103, No. 11, pp. 3213-3215 1981.

Flynn, Edwin H. et al. "Erythromycin. I. Properties and Degradation Studies", J. Am. Chem. Soc., vol. 76, pp. 3121-3131 1954.

Zunic, Melita et al. "MDP(Lysyl)GDP, a Nontoxic Muramyl Dipeptide Derivative, Inhibits Cytokine Production by Activated Macrophages and Protects Mice from Phorbol Ester- and Oxazolone-Induced Inflammation", J. Invest. Dermatol., vol. 111, No. 1, pp. 77-82 1998.

Labro, M.T. "Anti-Inflammatory activity of macrolides: a new therapeutic potential?", Journal of Antimicrobial Chemotherapy, vol. 41, suppl. B, pp. 37-46 1998.

(Continued)

*Primary Examiner*—Elli Peselev
(74) *Attorney, Agent, or Firm*—Oblon, Spivak, McClelland, Maier & Neustadt, P.C.

(57) ABSTRACT

Macrolide compounds lacking cladinose in position 3 having antiinflammatory activity and substantially free of antibiotic properties, pharmaceutically acceptable salts thereof, and pharmaceutical compositions containing them as active ingredient.

20 Claims, No Drawings

OTHER PUBLICATIONS

Mikasa, Keiichi et al. "The anti-inflammatory effect of erythromycin in zymosan-induced peritonitis of mice", Journal of Antimicrobial Chemotherapy, vol. 30, pp. 339-348 1992.

Abdelghaffar, H. et al. "Comparison of various macrolides on stimulation of human neutrophil degranulation in vitro", Journal of Antimicrobial Chemotherapy, vol. 38, pp. 81-93 1996.

Labro, M.T. et al. "Comparison of the in-vitro effect of several macrolides on the oxidative burst of human neutrophils", Journal of Antimicrobial Chemotherapy, vol. 24, pp. 561-572 1989.

Konno, Shin-ichi et al. "Inhibition of Human T-Lymphocyte Activation by Macrolide Antibiotic. Roxithromycin", Life Sciences, vol. 51, pp. PL231-PL236 1992.

Jorgensen, James H. et al. "Antibacterial Susceptibility Tests: Dilution and Disk Diffusion Methods", Manual of Clinical Microbiology, 7th edition, pp. 1526-1543 1999.

Sigal, Jr. Max V. et al. "Erythromycin. VI. Degradation Studies", J. Am. Chem. Soc., vol. 78, pp. 388-395 1956.

Miyatake, H. et al. "Erythromycin Reduces the Severity of Bronchial Hyperresponsiveness in Asthma", Chest, vol. 99, pp. 670-673 1991.

Tamaoki, Jun et al. "Effect of Erythromycin on Endotoxin-Induced Microvascular Leakage in the Rat Trachea and Lungs", Am. J. Respir. Crit. Care Med., vol. 151, pp. 1582-1588 1995.

Gasc, Jean-Claude et al. "New Ether Oxime Derivatives of Erythromycin A: A Structure-Activity Relationship Study", Journal of Antibiotics, vol. 44, No. 3, pp. 313-330 1991.

Abdelghaffar, Houria et al. "Erythromycin A-Derived Macrolides Modify the Functional Activities of Human Neutrophils by Altering the Phospholipase D-Phosphatidate Phosphohydrolase Transduction Pathway", Journal of Immunology, vol. 159, pp. 3995-4005 1997.

Jaffe, Adam et al. "Long-term azithromycin may improve lung function in children with cystic fibrosis", The Lancet, vol. 351, p. 420 1998.

O'Neil, Maryadele J. et al. "Erythromycin", The Merck Index: An Encyclopedia of Chemicals, Drugs, and Biologicals, 13th edition, No. 3714, pp. 654-655 2001.

Koyama, Hiroshi et al. "Erythromycin and diffuse panbronchiolitis", Thorax, vol. 52, pp. 915-918 1997.

* cited by examiner

MACROLIDE COMPOUNDS ENDOWED WITH ANTIINFLAMMATORY ACTIVITY

This application is a 371 of PCT/EP03/08448 filed Jul. 29, 2003.

DESCRIPTION

The present invention relates to macrolide compounds endowed with antiinflammatory activity, and more particularly relates to macrolide derivatives lacking cladinose in position 3, with antiinflammatory activity, to pharmaceutically acceptable salts thereof and to pharmaceutical compositions containing them as active ingredient.

It is known that many antibiotics, in particular the class of erythromycin-based macrolides having 14 ring atoms, have antiinflammatory properties in addition to their antibacterial activity [Clin. Immunother., (1996), 6, 454-464].

Erythromycin is a natural macrolide (The Merck Index, 13th Edition, No. 3714, p. 654) that has been of very broad clinical use in the treatment of infections caused by Gram-positive bacteria, a number of Gram-negative bacteria and mycoplasms.

Recently, the interest of the scientific community has turned towards the antiinflammatory and immunomodulatory properties of erythromycin and derivatives thereof [Journal of Antimicrobial Chemotherapy, (1998), 41, Suppl. B, 37-46].

This activity is well documented both in clinical studies and in in vivo and in vitro experiments.

For example, macrolides have been found to be effective in the treatment of inflammatory diseases such as panbronchiolitis [Thorax, (1997), 52, 915-918], bronchial asthma [Chest, (1991), 99, 670-673] and cystic fibrosis [The Lancet, (1998), 351, 420], both in animal models of inflammation, for instance zymosan-induced peritonitis in mice [Journal of Antimicrobial Chemotherapy, (1992), 30, 339-348] and endotoxin-induced accumulation of neutrophils in rat trachea [Antimicrobial Agents and Chemotherapy, (1994) 38, 1641-1643], and in in vitro studies on immune system cells, such as neutrophils [The Journal of Immunology, (1997), 159, 3395-4005] and T-lymphocytes [Life Sciences, (1992), 51, PL 231-236] or on the modulation of cytokines, such as interleukin 8 (IL-8) [Am. J. Respir. Crit. Care Med., (1997), 156, 266-271] or interleukin 5 (IL-5) [patent application EP 0 775 489 and EP 0 771 564, in the name of Taisho Pharmaceutical Co., Ltd].

The administration of macrolide compounds to asthmatic individuals is accompanied by a reduction in bronchial hypersecretion and hypersensitivity (Inflammation, Vol. 20, No. 6, 1996) consequent to their interaction with the neutrophils; this interaction is thought to prevent many bioactive lipids, involved in the pathogenesis of bronchial asthma, from expressing their proinflammatory membrane-destabilizing activity.

The particular therapeutic efficacy of macrolide compounds in diseases where conventional antiinflammatory drugs, for instance corticosteroids, have been found to be ineffective [Thorax, (1997), 52, 915-918, already cited] justifies the great interest in this new potential class of antiinflammatories.

However, the fact that conventional macrolide compounds have strong antibacterial activity does not allow their broader use in the chronic treatment of inflammatory processes not caused by pathogenic microorganisms, since this could give rise to the rapid development of resistant strains.

It would therefore be desirable to have available new substances of macrolide structure that show antiinflammatory activity and that are simultaneously free of antibiotic properties.

For greater clarity, the formula of erythromycin is given, wherein is indicated the numbering adopted in the present patent application.

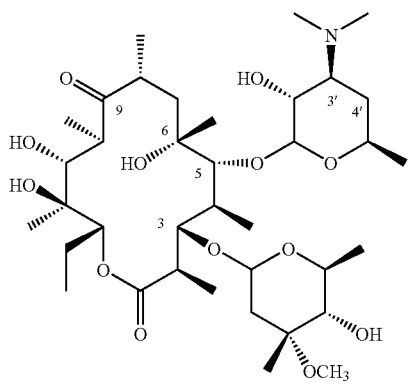

Many classes of erythromycin compounds endowed with antibacterial activity and characterized by greater acid stability and thus better pharmacokinetic properties are described in the literature.

Patent application WO 96/18633 in the name of Zambon Group discloses 9-[O-(aminoalkyl)oxime] erythromycin A compounds endowed with antibiotic activity against Gram-positive and Gram-negative microorganisms.

Ketolides, derived from erythromycin, modified in position 3' and 6-O-substituted, used in the treatment of bacterial infections, are disclosed in patent application WO 99/16779 in the name of Abbott Laboratories.

9-Oximino erythromycin compounds' esterified in position 3 and 3'-modified, which are useful as antibacterial and antiulcer agents, are disclosed in patent application JP 2001181294 (Hokuriku Pharmaceutical Co.).

Among the macrolide compounds described in the literature, few are 3'-desdimethylamino-9-oximino derivatives.

Patent application EP 0 254 534 (Robinson, William S.) claims a very broad class of macrolide compounds, among which are disclosed erythronolide A 9-O-methyloxime and 9-oximino derivatives of erythromycin A, including 3'-desdimethylamino-3',4'-dehydroerythromycin A 9-O-methyloxime.

The abovementioned patent application claims compounds having antiviral activity.

3'-Desdimethylamino-3',4-dehydroerythromycin A 9-oxime and erythronide A 9-oxime are disclosed in U.S. Pat. No. 3,928,387 (Hoffmann-La Roche Inc.) as intermediates that are useful for preparing the antibiotic 1745A/X.

A number of classes of erythromycin compounds endowed with antiinflammatory activity are described in the literature.

For example, erythromycin compounds modified in positions 3, 9, 11 and 12 are claimed, for example, in the abovementioned European patent applications in the name of Taisho, as potent inhibitors of IL-5 synthesis.

The use of erythromycin as an antiinflammatory that acts by reducing the release of interleukin 1 via inhibition of the mammalian glycoprotein mdr-P is claimed in patent application WO 92/16226 in the name of Smith-Kline Beecham Corporation.

3'-Desdimethylamino-9-oximino macrolide compounds endowed with antiinflammatory activity and lacking antibiotic activity are disclosed in patent application WO 00/42055 in the name of Zambon Group.

An effective contribution to the antiinflammatory activity exerted by macrolide compounds is traceable to the changes made by them to a number of metabolic functions of neutrophils.

In particular, in a number of studies, it has been shown that macrolide compounds intervene in exocytosis [Journal of Antimicrobial Chemotherapy, 1996, 38, 81] and in the production of oxidizing substances by the polymorphonuclear leukocytes (PMNL) [Journal of Antimicrobial Chemotherapy, 1989, 24, 561].

The role of the key structural element in modulating the abovementioned metabolic-functional activities of neutrophils has been attributed to the presence of L-cladinose in position 3 on the ring of the macrolide compounds [The Journal of Immunology, 1997, 159, 3395-4005, already cited].

The action of the sugar, according to the article mentioned above, may be linked either to the importance of this sugar in the cellular uptake of the macrolide compounds, or to its interaction with a cellular target involved in both the metabolic activities of neutrophils.

In confirmation of this, this neutral sugar L-cladinose, independently of its inclusion in the larger macrolide structure, has been described as being endowed with pronounced antiinflammatory activity.

Pharmaceutical formulations containing cladinose or L-cladinose as a medicinal product for treating inflammatory conditions are described in international patent application No. WO 97/00684 in the name of Roussel Uclaf.

We have now found, surprisingly, that by removing the cladinose in position 3 from macrolide derivatives, compounds endowed with antiinflammatory activity and substantially free of antibiotic properties are obtained.

It is therefore an object of the present invention to provide compounds of formula

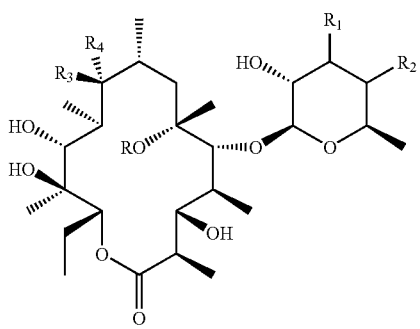

(I)

wherein

R is a hydrogen atom or a methyl group;

$R_1$ is a hydrogen atom, an N,N-di($C_1$-$C_3$)alkylamino group, an N,N-di($C_1$-$C_3$)alkylamino-N-oxide group, an N-($C_1$-$C_3$)alkyl-N-benzylamino group, an N-($C_1$-$C_4$)acyl-N-($C_1$-$C_3$)alkylamino group, an N-[N,N-dimethylamino($C_1$-$C_4$)alkylamino]acetyl-N-($C_1$-$C_3$)alkylamino group or a chain of formula

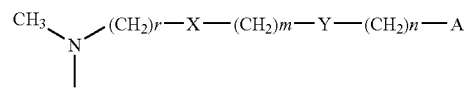

wherein

A is a hydrogen atom, a phenyl or a five- or six-membered heteroaryl ring having from one to three hetero atoms selected from nitrogen, oxygen and sulphur;

X is O, S, SO, $SO_2$, and $NR_6$, and $R_6$ is a hydrogen atom, a linear or branched $C_1$-$C_3$ alkyl, a $C_1$-$C_3$ alkoxycarbonyl group or a benzyloxycarbonyl group;

Y is a $C_6H_4$ group, a five- or six-membered heteroaryl ring having from one to three hetero atoms selected from nitrogen, oxygen and sulphur or is O, S, SO, $SO_2$ or $NR_6$ where $R_6$ has the meanings given above;

r is an integer from 1 to 3;

m is an integer from 1 to 6;

n is an integer from 0 to 2;

or $R_1$ forms a bond together with $R_2$;

$R_2$ is a hydrogen atom or forms a bond together with $R_1$;

$R_3$ is a hydroxy-group or forms a group $=$N—O—$R_5$ together with $R_4$, and $R_5$ is a hydrogen atom, a linear or branched $C_1$-$C_5$ alkyl, a benzyl optionally substituted with one or two substituents selected from nitro, hydroxy, carboxy, amino, linear or branched $C_1$-$C_5$ alkyl, $C_1$-$C_4$ alkoxycarbonyl groups, aminocarbonyl groups or cyano groups or a chain of formula

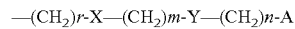

wherein r, m, n, X, Y and A have the meanings given above;

$R_4$ is a hydrogen atom or forms a group $=$N—O—$R_5$ together with $R_3$, and $R_5$ has the meanings given above;

and the pharmaceutically acceptable salts thereof, provided, however, that $R_1$ is not a dimethylamino group when $R_3$ is hydroxy, and both $R_2$ and $R_4$ are a hydrogen atom.

Both the compounds of formula I wherein R is a hydrogen atom or a methyl group, $R_1$ is a dimethyl-amino group, $R_3$ is hydroxy, $R_2$ and $R_4$ are a hydrogen atom, are known as chemical entities. Namely, the compound wherein R is a hydrogen atom, $R_1$ is a dimethyl-amino group, $R_3$ is hydroxy, $R_2$ and $R_4$ are a hydrogen atom, has been disclosed by Max V. Sigal and al., J. Am. Chem. Soc. 1956, 78, 388-395, as a degradation product of erythromycin A. Additionally, both the compounds wherein R is a hydrogen atom or a methyl group, $R_1$ is a dimethyl-amino group, $R_3$ is hydroxy, $R_2$ and $R_4$ are a hydrogen atom, have been disclosed in EP-A-0 941 998 as starting products in the preparation of macrolides endowed with antibiotic activity.

Their antiflammatory activity, however, has not been disclosed so far. Hence, they are still new as antiinflammatory drugs.

The oximes of formula I have Z or E configuration. The compounds of formula I are antiinflammatory macrolides lacking antibiotic activity and are therefore useful in the treatment and prophylaxis of inflammatory diseases also when R is a hydrogen atom or a methyl group, $R_1$ is a dimethyl-amino group, $R_3$ is hydroxy, and both $R_2$ and $R_4$ are a hydrogen atom.

The term "linear or branched $C_1$-$C_5$ alkyl" is intended to mean a group selected from methyl, ethyl, n-propyl, isopropyl, n-butyl, isobutyl, sec-butyl, tert-butyl, n-pentyl and isopentyl.

The expression "five- or six-membered heteroaryl ring having from one to three hetero atoms selected from nitrogen, oxygen and sulphur" is intended to mean heterocycle rings such as pyrrole, thiophene, furan, imidazole, pyrazole, thiazole, isothiazole, isoxazole, oxazole, pyridine, pyrazine, pyrimidine, pyridazine, triazole or thiadiazole.

It will be apparent to those skilled in the art that the substitution of the heteroaryl rings with partially or totally saturate forms thereof, as well as the presence of substituents on the aromatic (phenyl or heteroaryl) rings envisaged in the meanings of A and Y, gives rise to compounds that fall within the scope of the invention.

Preferred compounds of formula I are those wherein R, $R_2$, $R_3$, $R_4$, $R_5$ and $R_6$ have the meanings given in formula I and $R_1$ is a hydrogen atom, an N—($C_1$-$C_3$)alkyl-N-methylamino group, an N-($C_1$-$C_3$)alkyl-N-methylamino-N-oxide group, an N-benzyl-N-methylamino group, an N-($C_1$-$C_4$)acyl-N-methylamino group, an N-[N,N-dimethylamino($C_1$-$C_4$)alkylamino]acetyl-N-methylamino group or a chain of formula $$CH_3\diagdown_{N}\diagup(CH_2)r-X-(CH_2)m-Y-(CH_2)n-A$$

wherein
A is a hydrogen atom, a phenyl or a five- or six-membered heteroaryl ring having from one to three hetero atoms selected from nitrogen, oxygen and sulphur;
X is O or $NR_6$ and $R_6$ is a hydrogen atom or a linear or branched $C_1$-$C_3$ alkyl;
Y, when n is 0, is a $C_6H_4$ group or a five- or six-membered heteroaryl ring having from one to three hetero atoms selected from nitrogen, oxygen and sulphur; or, when n is other than 0, is O or $NR_6$ and $R_6$ is a hydrogen atom or a linear or branched $C_1$-$C_3$ alkyl;
r is an integer from 1 to 3;
m is the integer 1 or 2;
n is an integer from 0 to 2;
or $R_1$ forms a bond together with $R_2$.

In this group, the compounds that are even more preferred are those wherein $R_1$ is a hydrogen atom, an N,N-dimethylamino-N-oxide group, an N-benzyl-N-methylamino group, an N-acetyl-N-methylamino group, an N-[N,N-dimethylamino($C_1$-$C_2$)alkyl amino]acetyl-N-methylamino group or a chain of formula $$CH_3\diagdown_{N}\diagup(CH_2)r-X-(CH_2)m-Y-(CH_2)n-A$$

wherein
A is a hydrogen atom, a phenyl or a five- or six-membered heteroaryl ring selected from pyrrole, thiophene, furan, imidazole, oxazole, thiazole, pyridine, pyrimidine, triazole and thiadiazole;
X is O or $NR_6$ and $R_6$ is a hydrogen atom;
Y is, when n is 0, a $C_6H_4$ group or a five- or six-membered heteroaryl ring selected from pyrrole, thiophene, furan, imidazole, oxazole, thiazole, pyridine, pyrimidine, triazole and thiadiazole; or, when n is 1, $NR_6$ and $R_6$ is a hydrogen atom;
r is an integer from 1 to 3;
m is the integer 1 or 2;
n is the integer 0 or 1;
or $R_1$ forms a bond together with $R_2$.

Further compounds which belongs to this group and are even more preferred are those wherein $R_1$ is a hydrogen atom, an N,N-dimethylamino-N-oxide group, an N-benzyl-N-methylamino group, an N-acetyl-N-methylamino group, an N-[N,N-dimethylaminoethylamino]acetyl-N-methylamino group or a chain of formula $$CH_3\diagdown_{N}\diagup(CH_2)r-X-(CH_2)m-Y-(CH_2)n-A$$

wherein
A is a hydrogen atom, a phenyl or a heteroaryl ring selected from thiophene, furan, thiazole, pyridine and triazole;
X is $NR_6$ and $R_6$ is a hydrogen atom;
Y is, when n is 0, a $C_6H_4$ group or a heteroaryl ring selected from thiophene, furan, thiazole, pyridine and triazole; or, when n is 1, $NR_6$ and $R_6$ is a hydrogen atom;
or $R_1$ forms a bond together with $R_2$.

Further preferred compounds are those wherein R, $R_1$, $R_2$ and $R_6$ have the meaning already given in formula I, $R_3$ is a hydroxy group and $R_4$ is a hydrogen atom provided, however, that $R_1$ is not a dimethylamino group.

Compounds that are preferred within this group are those wherein $R_1$ is a hydrogen atom, an N-($C_1$-$C_3$)alkyl-N-methylamino group, an N-($C_1$-$C_3$)alkyl-N-methylamino-N-oxide group, an N-benzyl-N-methylamino group, an N—($C_1$-$C_4$)acyl-N-methylamino group, an N-[N,N-dimethyl amino($C_1$-$C_4$)alkylamino]acetyl-N-methylamino group or a chain of formula $$CH_3\diagdown_{N}\diagup(CH_2)r-X-(CH_2)m-Y-(CH_2)n-A$$

wherein
A is a hydrogen atom, a phenyl or a five- or six-memberedl heteroaryl ring having from, one to three hetero atoms selected from nitrogen, oxygen and sulphur;
X is O or $NR_6$ and $R_6$ is a hydrogen atom or a linear or branched $C_1$-$C_3$ alkyl;
Y, when n is 0, is a $C_6H_4$ group or a five- or six-membered heteroaryl ring having from one to three hetero atoms selected from nitrogen, oxygen and sulphur; or, when n is other than 0, is O or $NR_6$ and $R_6$ is a hydrogen atom or a linear or branched $C_1$-$C_3$ alkyl;
r is an integer from 1 to 3;
m is the integer 1 or 2;
n is an integer from 0 to 2;
or $R_1$ forms a bond together with $R_2$.

Compounds that are even more preferred within this group are those wherein $R_1$ is a hydrogen atom, an N,N-dimethylamino-N-oxide group, an N-benzyl-N-methylamino group, an N-acetyl-N-methylamino group, an N-[N,N-dimethylamino($C_1$-$C_2$)alkyl amino]acetyl-N-methylamino group or a chain of formula

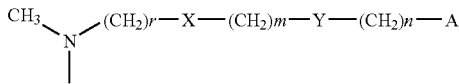

wherein
A is a hydrogen atom, a phenyl or a five- or six-membered heteroaryl ring selected from pyrrole, thiophene, furan, imidazole, oxazole, thiazole, pyridine, pyrimidine, triazole and thiadiazole;
X is O or $NR_6$ and $R_6$ is a hydrogen atom;
Y is, when n is 0, a $C_6H_4$ group or a five- or six-membered heteroaryl ring selected from pyrrole, thiophene, furan, imidazole, oxazole, thiazole, pyridine, pyrimidine, triazole and thiadiazole; or, when n is 1, $NR_6$ and $R_6$ is a hydrogen atom;
r is an integer from 1 to 3;
m is the integer 1 or 2;
n is the integer 0 or 1;
or $R_1$ forms a bond together with $R_2$.

Compounds of this group that are even more preferred are those wherein $R_1$ is a hydrogen atom, an N,N-dimethylamino-N-oxide group, an N-benzyl-N-methylamino group, an N-acetyl-N-methylamino group, an N-[N,N-dimethylaminoethylamino] acetyl-N-methylamino group or a chain of formula

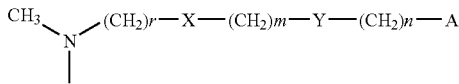

wherein
A is a hydrogen atom, a phenyl or a heteroaryl ring selected from thiophene, furan, thiazole, pyridine and triazole;
X is NR and $R_6$ is a hydrogen atom;
Y is, when n is 0, a $C_6H_4$ group or a heteroaryl ring selected from thiophene, furan, thiazole, pyridine and triazole; or, when n is 1, $NR_6$ and $R_6$ is a hydrogen atom;
or $R_1$ forms a bond together with $R_2$.

Among the compounds wherein R, $R_1$ and $R_2$ have the meanings already given in formula I and $R_3$ forms a group =N—O—$R_5$ together with $R_4$, the ones that are preferred are those wherein $R_5$ is a hydrogen atom, a linear or branched ($C_1$-$C_3$)alkyl, a benzyl optionally substituted with one or two substituents selected from nitro, hydroxy, carboxy, amino, linear or branched ($C_1$-$C_3$) alkyl and cyano or a chain of formula

wherein
A is a hydrogen, atom, a phenyl or a five- or six-membered heteroaryl ring having from one to three hetero atoms selected from nitrogen, oxygen and sulphur;
X is O or $NR_6$ and $R_6$ is a hydrogen atom or a linear or branched $C_1$-$C_3$ alkyl;
Y, when n is 0, is a $C_6H_4$ group or a five- or six-membered heteroaryl ring having from one to three hetero atoms selected from nitrogen, oxygen and sulphur; or, when n is other than 0, is O or $NR_6$ and $R_6$ is a hydrogen atom or a linear or branched $C_1$-$C_3$ alkyl;

r is the integer 1 or 2;
m is an integer from 1 to 6;
n is an integer from 0 to 2.

The compounds that are preferred within this group of compounds of formula I are those wherein $R_5$ is a hydrogen atom, a methyl, a benzyl or a chain of formula

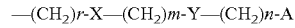

wherein
A is a hydrogen atom, a phenyl or a five- or six-membered heteroaryl ring selected from pyrrole, thiophene, furan, imidazole, oxazole, thiazole, pyridine, pyrimidine, triazole and thiadiazole;
X is O or $NR_6$ and $R_6$ is a hydrogen atom;
Y is, when n is 0, a $C_6H_4$ group or a five- or six-membered heteroaryl ring selected from pyrrole, thiophene, furan, imidazole, oxazole, thiazole, pyridine, pyrimidine, triazole and thiadiazole; or, when n is 1, $NR_6$ and $R_6$ is a hydrogen atom;
r is 2;
m is an integer from 1 to 6;
n is the integer 0 or 1.

Compounds of this group that are even more preferred are those of formula I wherein $R_5$ is a hydrogen atom, a methyl, a benzyl or a chain of formula

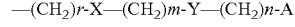

wherein
A is a hydrogen atom, a phenyl or a heteroaryl ring selected from thiophene, furan, thiazole, pyridine and triazole;
X is $NR_6$ and $R_6$ is a hydrogen atom;
Y is, when n is 0, a $C_6H_4$ group or a heteroaryl ring selected from thiophene, furan, thiazole, pyridine and triazole; or, when n is 1, $NR_6$ and $R_6$ is a hydrogen atom.

Compounds that are also preferred are those wherein R and $R_2$ have the meanings already given in formula I; $R_1$ is a hydrogen atom, an N-($C_1$-$C_3$)alkyl-N-methylamino group, an N-($C_1$-$C_3$)alkyl-N-methylamino-N-oxide group, an N-benzyl-N-methylamino group, an N-($C_1$-$C_4$)acyl-N-methylamino group, an N-[N,N-dimethylamino($C_1$-$C_4$)alkylamino]acetyl-N-methylamino group or a chain of formula

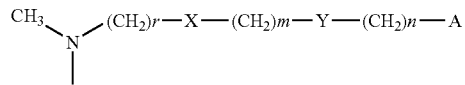

wherein
A is a hydrogen atom, a phenyl or a five- or six-membered heteroaryl ring selected from pyrrole, thiophene, furan, imidazole, oxazole, thiazole, pyridine, pyrimidine, triazole and thiadiazole;
X is O or $NR_6$ and $R_6$ is a hydrogen atom;
Y is, when n is 0, a $C_6H_4$ group or a five- or six-membered heteroaryl ring selected from pyrrole, thiophene, furan, imidazole, oxazole, thiazole, pyridine, pyrimidine, triazole and thiadiazole; or, when n is 1, $NR_6$ and $R_6$ is a hydrogen atom;
r is an integer from 1 to 3;
m is the integer 1 or 2;
n is the integer 0 or 1;
or $R_1$ forms a bond together with $R_2$;
simultaneously, $R_3$ forms a group =N—O—$R_5$ together with $R_4$, wherein $R_5$ is a hydrogen atom, a linear or branched ($C_1$-$C_3$) alkyl, a benzyl optionally substituted with one or two substituents selected from nitro, hydroxy, carboxy, amino, linear or branched ($C_1$-$C_3$)alkyl and cyano or a chain of formula

wherein
A is a hydrogen atom, a phenyl or a five- or six-membered heteroaryl ring having from one to three hetero atoms selected from nitrogen, oxygen and sulphur;
X is O or $NR_6$ and $R_6$ is a hydrogen atom or a linear or branched $C_1$-$C_3$ alkyl;
Y, when n is 0, is a $C_6H_4$ group or a five- or six-membered heteroaryl ring having from one to three hetero atoms selected from nitrogen, oxygen and sulphur; or, when n is other than 0, is O or $NR_6$ and $R_6$ is a hydrogen atom or a linear or branched $C_1$-$C_3$ alkyl;
r is the integer 1 or 2;
m is an integer from 1 to 6;
n is an integer from 0 to 2.

The compounds that are preferred within this group of compounds of formula I are those wherein $R_5$ is a hydrogen atom, a methyl, a benzyl or a chain of formula

wherein
A is a hydrogen atom, a phenyl or a five- or six-membered heteroaryl ring selected from pyrrole, thiophene, furan, imidazole, oxazole, thiazole, pyridine, pyrimidine, triazole and thiadiazole;
X is O or $NR_6$ and $R_6$ is a hydrogen atom;
Y is, when n is 0, a $C_6H_4$ group or a five- or six-membered heteroaryl ring selected from pyrrole, thiophene, furan, imidazole, oxazole, thiazole, pyridine, pyrimidine, triazole and thiadiazole; or, when n is 1, $NR_6$ and $R_6$ is a hydrogen atom;
r is 2;
m is an integer from 1 to 6;
n is the integer 0 or 1.

Compounds of this group that are even more preferred are those of formula I wherein $R_5$ is a hydrogen atom, a methyl, a benzyl or a chain of formula

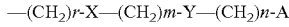

wherein
A is a hydrogen atom, a phenyl or a heteroaryl ring selected from thiophene, furan, thiazole, pyridine and triazole;
X is $NR_6$ and $R_6$ is a hydrogen atom;
Y is, when n is 0, a $C_6H_4$ group or a heteroaryl ring selected from thiophene, furan, thiazole, pyridine and triazole; or, when n is 1, $NR_6$ and $R_6$ is a hydrogen atom.

Compounds of this last group that are even more preferred are those of formula I wherein $R_1$ is a hydrogen atom, an N,N-dimethylamino group, an N,N-dimethylamino-N-oxide group, an N-benzyl-N-methylamino group, an N-acetyl-N-methylamino group, an N-[N,N-dimethylamino($C_1$-$C_2$)alkylamino]acetyl-N-methylamino group or a chain of formula

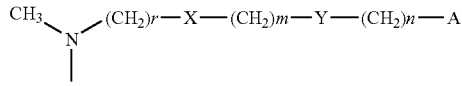

wherein
A is a hydrogen atom, a phenyl or a heteroaryl ring selected from thiophene, furan, thiazole, pyridine and triazole;
X is $NR_6$ and $R_6$ is a hydrogen atom;
Y is, when n is 0, a $C_6H_4$ group or a heteroaryl ring selected from thiophene, furan, thiazole, pyridine and triazole; or, when n is 1, $NR_6$ and $R_6$ is a hydrogen atom;
or $R_1$ forms a bond together with $R_2$.

It is an object of the present invention to provide the compounds of formula I having Z or E configuration of the possible oxime in position 9, with a preference for the latter compounds.

Examples of pharmaceutically acceptable salts of the compounds of formula I are salts with organic or mineral acids such as hydrogen chloride, hydrogen bromide, hydrogen iodine, nitric acid, sulphuric acid, phosphoric acid, acetic acid, tartaric acid, citric acid, benzoic acid, succinic acid and glutaric acid.

Specific examples of compounds of the present invention are those wherein R, $R_2$ and $R_4$ have the meanings given in formula 1, $R_1$ form is a bond together with $R_2$ or $R_1$ is a hydrogen atom, an N,N-dimethylamino-N-oxide group, an N-benzyl-N-methyl amino group, an N-acetyl-N-methylamino group, an N-[N,N-dimethyl aminoethylamino]acetyl-N-methylamino group, an N-methyl-N-3-[(2-thiazolylmethyl)amino]propylamino group, an N-2-[2-[(2-thiazolyl methyl)amino]ethylamino]ethyl-N-methylamino group or an N-2-[2-(benzylamino)ethylamino]ethyl-N-methylamino group, $R_3$ is a hydroxy group or forms a group =N—O—$R_5$ together with $R_4$, and $R_5$ is a hydrogen atom, a methyl, a benzyl, a 2-[2-[(2-thiazolylmethyl)amino]ethylamino]ethyl group, a 2-(benzylamino)ethyl group, a 2-[2-[(2-furylmethyl)amino] ethylamino]ethyl group, a 2-[2-[(3-furylmethyl)amino]ethylamino]ethyl group, a 2-[2-[(2-thienylmethyl)amino]ethylamino]ethyl group or a 2-[6-[(2-thiazolylmethyl)amino]hexylamino]ethyl group.

The compounds of formula I of the present invention, are prepared according to a synthesis pathway that involves the removal of the L-cladinose moiety in position 3 from compounds of formula

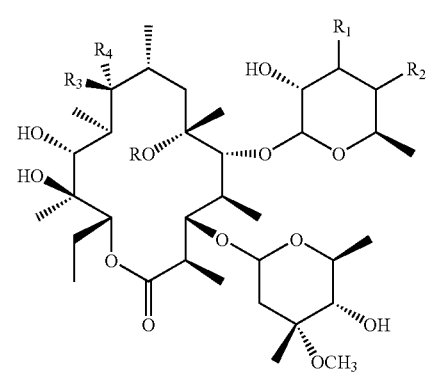

wherein
R, $R_1$, $R_2$, $R_3$ and $R_4$ have the meanings given for the compounds of formula I.

The removal of the cladinose moiety is preferably performed via an acid hydrolysis reaction catalyzed in the presence of a mineral acid, for instance sulphuric acid or hydrogen chloride, and a protic organic solvent, for instance water, methanol or ethanol.

The 9-hydroxy compounds that are intermediates of formula II are novel, with the exception of those wherein (i) $R_1$ is an N,N-dimethyl amino group, and (ii) R is a hydrogen atom and $R_1$ is an N,N-dimethylamino-N-oxide group.

For example, the 9-hydroxy compounds wherein R is a hydrogen atom or a methyl group and $R_1$ is an N,N-dimethyl amino group have been disclosed as antibacterial agents by R. Faghih et al., J. of Antibiotics 1990, 43, 1334-36.

The compounds of formula II are obtained from erythromycin A or 6-O-methylerythromycin A (common name: Clarithromycin) by action on the ketone group in position 9 and optionally on the dimethylamino group in position 3'. Preferably, the action is initially directed to the ketone group in position 9; this may be reduced to give a hydroxy compound or may be treated with reagents capable of producing oximino compounds that may subsequently be functionalized.

The possible modifications on the dimethylamino group in position 3' include oxidation, removal or demethylation and subsequent functionalization (alkylation and acylation).

It will be apparent to a person skilled in the art that, in order to avoid interference with functional groups that may be present in the three positions where structural modifications are to be made, it will be more or less convenient and appropriate to choose a given priority in the synthesis modifications to be performed.

Thus, for example, the possible functionalization of the oximino compounds may take place immediately after they have been synthesized, may be performed before or after the possible modification, whatever this may be, in position 3' or may be the final step of the synthesis.

As a further example, as regards the removal of the cladinose, this may be performed after the modifications to the ketone group in position 9, may follow or precede the possible functionalization of the oximino compounds in that position, may follow or precede the possible modification on the dimethylamino group or may terminate the synthesis process.

Preferably, the hydrolysis reaction of the sugar is performed after the modifications to the ketone group in position 9 on the macrolide ring to avoid the cladinose remaining in the reaction medium and requiring a subsequent separation from the final product rather than from synthesis intermediates; however, in general there are no interactions that would prevent the removal of cladinose in another intermediate step or at the end of the synthesis process.

These procedural choices will be dictated in each case by technical requirements aimed at optimizing the synthesis process of the product of interest.

Ways for performing the abovementioned structural modifications on the macrolides are described more clearly hereinbelow.

The oximes of erythromycin A, with Z or E configuration, are known. They are commercially available compounds and may be prepared via conventional technique's, for instance according to U.S. Pat. No. 3,478,014 in the name of Pliva or J. C. Gasc et al. (The Journal of Antibiotics; 44, 313-330, 1991) to give the compounds of formula

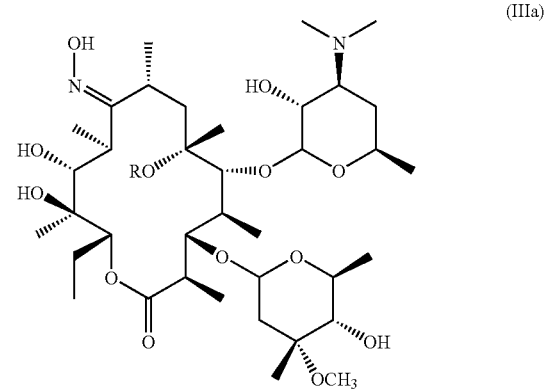

(IIIa)

wherein
R has the meanings given in formula I.

The hydroxy derivatives, in position 9, are compounds that are also known, which may be obtained, according to conventional techniques, via treatment of erythromycin A with reducing agents, for instance hydrides (sodium borohydride, lithium borohydride, sodium cyano boro hydride or lithium aluminium hydride) (Faghih, Journal of Antibiotics, 1990, 1334-1336) or via catalytic hydrogenation processes to give the compounds of formula

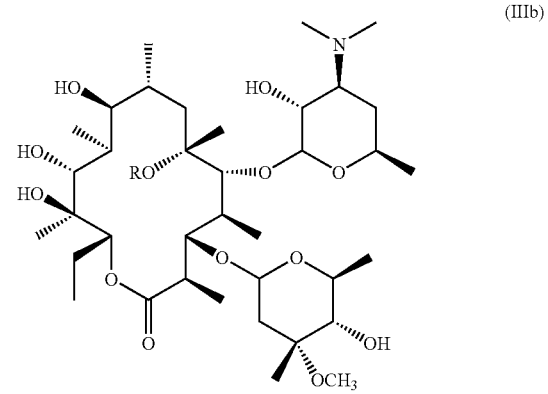

(IIIb)

wherein
R has the meanings given in formula I.

The compounds of formula I wherein $R_5$ is other than a hydrogen atom may be prepared by direct synthesis or by functionalization of the oxime in position 9 via conventional techniques.

Generally, the optional functionalization is performed by reaction with a compound of formula $$R_5'\text{-L} \tag{IV}$$

wherein
$R_5'$ has all the meanings of $R_5$ excluding hydrogen and L is a leaving group, preferably a chlorine or bromine atom or a mesyl group.

An alternative route that is particularly suitable for the preparation of compounds of formula I wherein $R_5$ is a chain of formula $$-(CH_2)r\text{-}X-(CH_2)m\text{-}Y-(CH_2)n\text{-}A$$

wherein

X, Y, A, r, m and n have the meanings given in formula I; involves the reaction of a compound of formula II, wherein $R_5$ is hydrogen and from which the cladinose has optionally already been removed, with an intermediate of formula

L-(CH$_2$)$r$-X—(CH$_2$)$m$-Y-Z    (V)

wherein

L, X, Y, m and n have the meanings already given and Z is a protecting group, for instance urethane (carbobenzyloxy groups, carboallyloxy groups or trichloroacetyloxycarbonyl groups);

to give the intermediate of formula

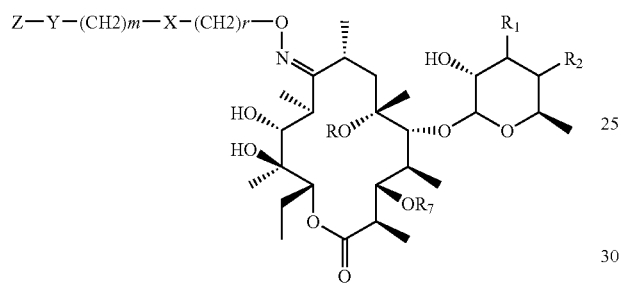

(VI)

wherein

R, $R_1$, $R_2$, X, Y, Z, r and m have the meanings already given and $R_7$ is a hydrogen atom or L-cladinose; which, after removal of the protecting group Z, is reacted with a compound of formula

A-(CH$_2$)$n$-L    (VII)

wherein A, L and n have the meanings already given, to give compounds of formula I.

Compounds of formula I wherein Y is NR$_6$ may be prepared according to the synthesis route given above, including the use of an aldehyde of formula

A-CHO    (VIII)

wherein A has the meanings already given;

in place of the intermediate of formula VII, after removal of the protecting group Z from the intermediate of formula VI.

The removal of the dimethylamino group is performed by oxidation, pyrolysis and possible reduction, according to known methods, for instance those described in international patent application WO 00/42055 in the name of Zambon Group or in U.S. Pat. No. 3,928,387 in the name of Hoffmann-La Roche Inc., both already cited.

It will be apparent to a person skilled in the art that, in order to avoid interference with functional groups that may be present in the substituent $R_5$, the removal of the dimethylamino group will preferably be performed on intermediates of formula

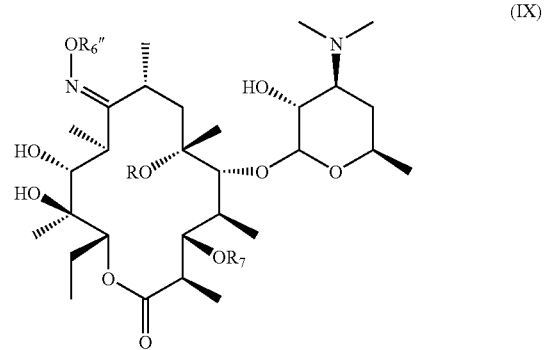

(IX)

wherein

R and $R_7$ have the meanings already given and $R_5''$ is a hydrogen atom or a linear or branched $C_1$-$C_5$ alkyl.

Oxidation gives the N-oxide compounds of formula

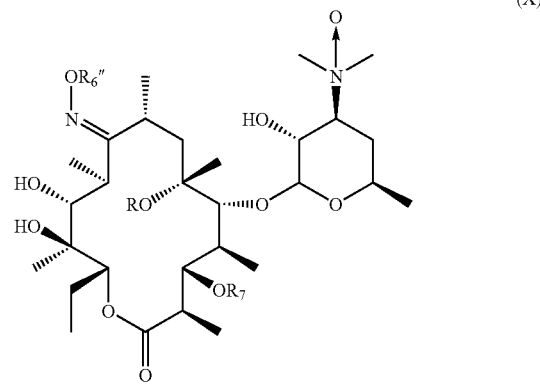

(X)

wherein

R, $R_5''$ and $R_7$ have the meanings already given;

which, by pyrolysis; optionally followed by reduction, lead respectively to the compounds of formulae

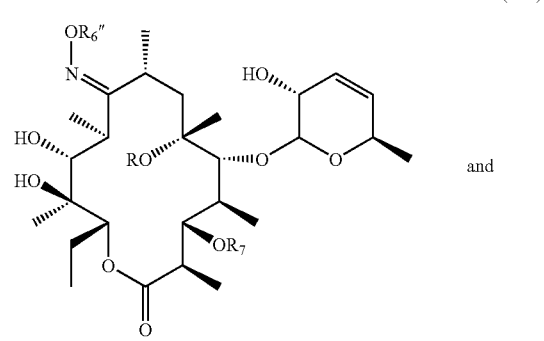

(XIa)

and

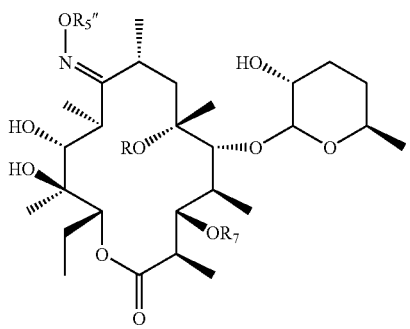

wherein

R, $R_5''$ and $R_7$ have the meanings already given.

The conversion into the corresponding N-oxides takes Place, according to a known method, by treatment with peracids, for instance hydrogen peroxide or meta-chloroperbenzoic acid in the presence of an organic solvent (U.S. Pat. No. 3,928,387, Hoffmann-La Roche Inc., already cited) (J. Am. Chem. Soc. 1954, 76, 3121).

The demethylation of the dimethylamino group in position 3' may be performed via conventional techniques, for instance treatment with sodium acetate and iodine in the presence of an organic solvent, as described in U.S. Pat. No. 3,725,385 in the name of Abbott Laboratories; the subsequent acylation or alkylation of the secondary amine thus obtained is performed according to the conventional synthesis techniques.

In addition, the compounds of formula I wherein $R_1=R_2=H$ may be prepared by reducing the corresponding compounds of formula I wherein $R_1$ and $R_2$ together form a bond.

An alternative synthesis for the 3',4'-dehydro-oximino derivatives of erythromycin A consists in working as described in U.S. Pat. No. 3,928,387 (Hoffmann-La Roche Inc., already cited) so as to obtain an intermediate compound of formula

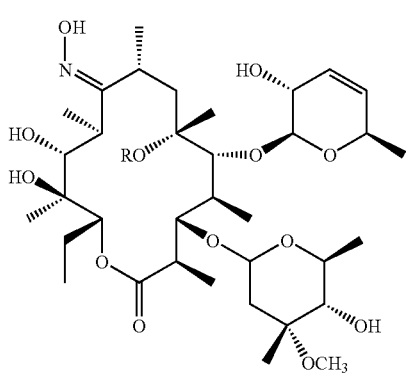

and thereafter, depending on compound of interest, the bond to the cladinose may be hydrolyzed and the oxime in position 9 may optionally be functionalized as described previously, and vice versa.

Macrolide compounds have been widely used therapeutically as antibacterial agents; in each case, clinical and experimental data indicate that they are involved in modulating the inflammatory response.

A substantial body of evidence, derived from both in vitro and in vivo studies, suggests that, besides inhibiting the release of cytokines, the modulatory effects of macrolide compounds are directed towards important cellular targets such as the lymphocytes and neutrophils.

These cells, in particular, are a first line of defence against pathogens, this function being expressed by means of phagocytosis, the release of hydrolytic enzymes and the production of toxic oxygen metabolytes.

Although neutrophils are essential in immune defence, it is known that an excessive, non-physiological release of oxidizing substances and of hydrolytic enzymes may be involved in many pathological conditions, for instance atherosclerosis, reperfusion ischaemia injury, rheumatoid arthritis, septic shock and chronic pulmonary inflammations such as ARDS (adult respiratory distress syndrome), COPD and asthma (inflammation and fever; Viera "Stvrtinová, Jan Jakubovsky and Ivan Húlin; Academic Electronic Press, 1995).

Treatment with erythromycin at low doses for long periods, is described as being effective in reducing bronchial hypersensitivity in asthmatic patients (Miyatake H. et al Chest, 1991, 99, 670-673, already cited).

In a further study, it was shown that the same treatment, in patients suffering from COPD, can significantly reduce the frequency and the risk of exacerbation, caused by acute: respiratory infections, of this disease (CHEST 2001, 120, 730-733).

The results obtained are not due to the antibiotic activity of the macrolide but to inhibition of the expression and the release of inflammatory cytokines.

This treatment, according to the article already cited, should preferably be restricted to patients at high risk of exacerbation of COPD on account of the potential risk of resistant pathogenic strains arising.

The compounds of formula I of the present invention, are endowed with antiinflammatory activity and lack antibiotic activity.

The pharmacological activity of the compounds of formula I was evaluated in models of cutaneous and pulmonary inflammation in comparison with known macrolide, compounds, such as erythromycin and azithromycin, which are endowed with both antiinflammatory activity and antibiotic activity.

The antiinflammatory activity was evaluated both via inhibition of PMA-induced oedema in mouse ear and via reduction of the LPS-induced accumulation of neutrophils in rat lungs.

In all the experiments, the compounds of the present invention were found to be highly active as antiinflammatory agents and the antiinflammatory activity was similar to or greater than that of the comparison compounds.

The antibiotic activity was evaluated in vitro via the ability to inhibit the growth of erythromycin-sensitive bacterial strains.

In addition, the compounds of the present invention show no antibiotic activity, as proved by the tests performed, and may therefore be used in chronic treatments of inflammatory processes without undesired resistance phenomena arising.

It is thus clear that the compounds of formula I, endowed with antiinflammatory activity and lacking antibiotic activity, may be used in the acute and chronic treatment and in the prophylaxis of inflammatory diseases, in particular diseases related to an impaired cellular functionality of neutrophils, for instance rheumatoid arthritis, reperfusion ischaemia injury, septic shock, atherosclerosis, ARDS, COPD and asthma.

The therapeutically effective amounts will depend on the age and the general physiological state of the patient, the route of administration and the pharmaceutical formulation used; the therapeutic doses will generally be between about 10 and 2000 mg/day and preferably between about 30 and 1500 mg/day.

The compounds of the present invention for use in the treatment and/or prophylaxis of the abovementioned diseases will preferably be used in a pharmaceutical form that is suitable for oral, rectal, sublingual, parenteral, topical, transdermal and inhalation administration.

It is therefore a further object of the present invention to provide pharmaceutical formulations containing a therapeutically effective amount of, a compound of formula I or a salt thereof together with a pharmaceutically acceptable vehicle.

The pharmaceutical formulations of the present invention may be liquid, suitable for oral and/or parenteral administration, for instance drops, syrups, solutions, injectable solutions ready to use or prepared via dilution of a lyophilizate, but preferably solid, for instance tablets, capsules, granules, powders, pellets, pessaries, suppositories, creams, pomades, gels or ointments; or alternatively solutions, suspensions, emulsions or other forms suitable for inhalation and transdermal administration.

Depending on the type of formulation, these formulations will contain, besides a therapeutically effective amount of one (or more) compound(s) of formula I, solid or liquid excipients or diluents for pharmaceutical use and optionally other additives normally used in the preparation of pharmaceutical formulations, for instance thickeners, aggregating agents, lubricants disintegrants, flavourings and colourings.

The pharmaceutical formulations of the invention may be produced according to conventional techniques.

The examples below are now given for the purpose of illustrating the present invention more clearly.

The chemical structures and the analytical characterization of the intermediates as well as of compounds of formula I are given in the following table.

Intermediate 25

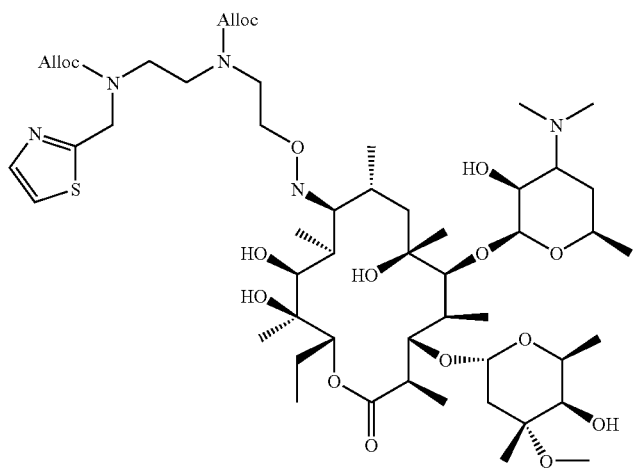

CDCl$_3$: 7.72 (m, 1H, Th); 7.30 (m, 1H, Th); 5.8-6.1 (m, 2H, CH=C allyl); 3.30 (s, 3H, H$_7$''); 2.31 (s, 6H, Me$_2$N); 0.85 (t, 3H, J=7.3, H$_{15}$).

Intermediate 26

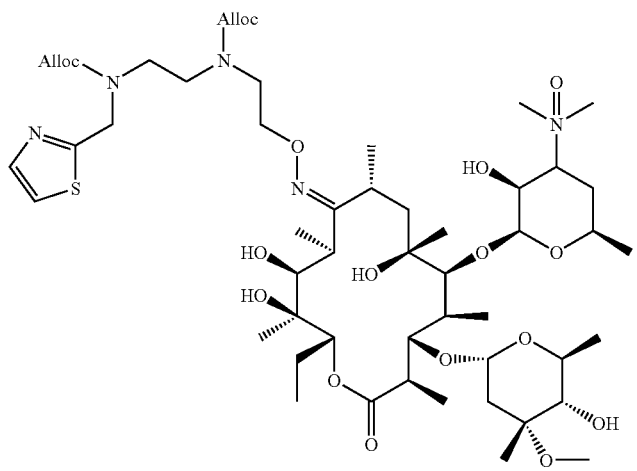

CDCl$_3$: 7.72 (m, 1H, Th); 7.30 (m, 1H, Th); 5.8-6.1 (m, 2H, CH=C); 3.36 (s, 3H, H$_7$''); 3.21 (s, 6H, Me$_2$N[O]); 0.84 (t, 3H, J=7.1, H$_{15}$).

| | | |
|---|---|---|
| Intermediate 28 | 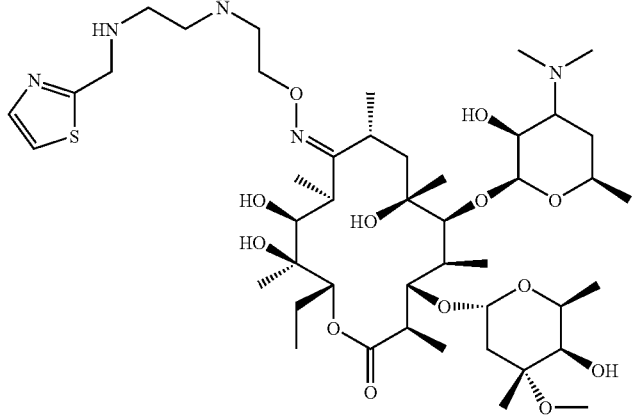 | CDCl$_3$: 7.69 (m, 1H, Th); 7.26 (m, 1H, Th); 4.82 (d, 1H, J=4.5, H$_1$"); 4.37 (d, 1H, J=7.2, H$_1$'); 3.92 (s, 1H, H$_{11}$); 3.28 (s, 3H, H$_7$"); 2.28 (s, 6H, Me$_2$N); 0.82 (t, 3H, J=7.3, H$_{15}$). |
| Compound 19 | 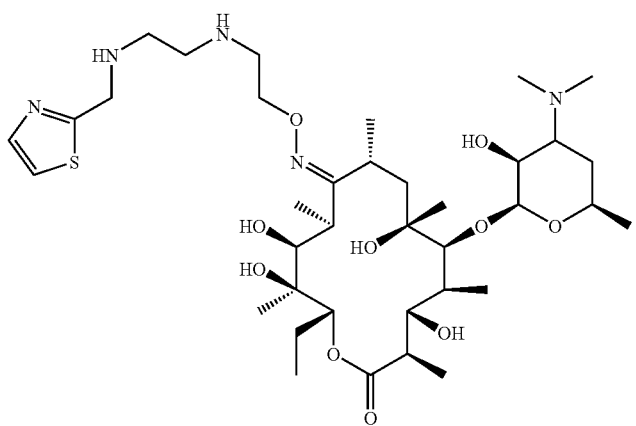 | CDCl$_3$: 7.75 (m, 1H, Th); 7.34 (m, 1H, Th); 5.17-5.22 (m, 1H, H$_{13}$); 4.70 (m, 1H, H$_1$'); 4.33 (m, 2H, CH$_2$Th); 2.83 (s, 6H, Me$_2$N); 1.47 (s; 3H, H$_{18}$); 0.76 (t, 3H, J=6.7, H$_{15}$). |
| Intermediate 29 | 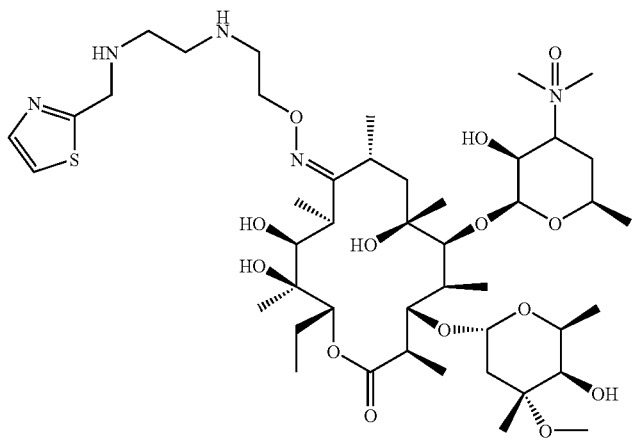 | CDCl$_3$: 7.70 (m, 1H, Th); 7.28 (m, 1H, Th); 4.84 (d, 1H, J=4.5, H$_1$"); 4.50 (d, 1H, J=6.9, H$_1$'); 3.92 (s, 1H, H$_{11}$); 3.34 (s, 3H, H$_7$"); 3.19 (s, 6H, Me$_2$N[O]); 0.83 (t, 3H, J=7:4, H$_{15}$). |

| | | |
|---|---|---|
| Compound 20 | 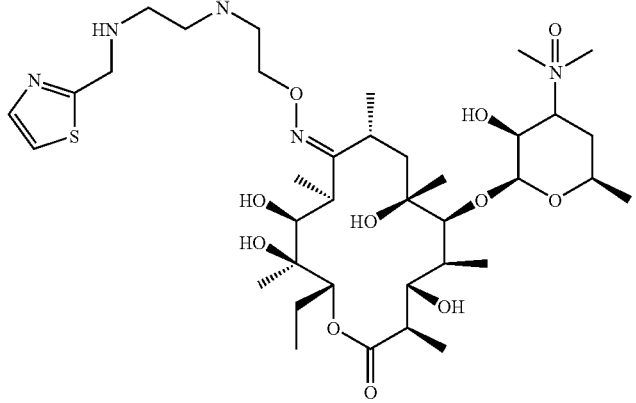 | CDCl$_3$: 7.72 (m, 1H, Th); 7.30 (m, 1H, Th); 5.19-5.23 (m, 1H, H$_{13}$); 4.48 (d, 1H, J=7.0, H$_1$'); 4.2 (m, 2H, CH$_2$Th); 3.94 (s, 1H, H$_{11}$); 3.16 and 3.20 (2s, 6H, Me$_2$N[O]); 1.42 (s, 3H, H$_{18}$); 0.83 (t, 3H, J=7.4, H$_{15}$). |
| Compound 21 | 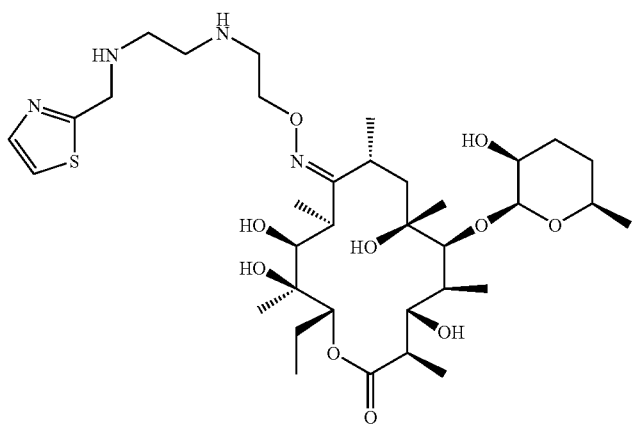 | CDCl$_3$: 7.75 (m, 1H, Th); 7.31 (m, 1H, Th); 5.17-5.31 (m, 1H, H$_{13}$); 4.29 (d, 1H, J=7.4, H$_1$'); 4.20 (m, 2H, CH$_2$Th); 3.89 (s, 1H, H$_{11}$); 1.37 (s, 3H, H$_{18}$); 0.82 (t, 3H, J=7.4, H$_{15}$). |
| Intermediate 35 | 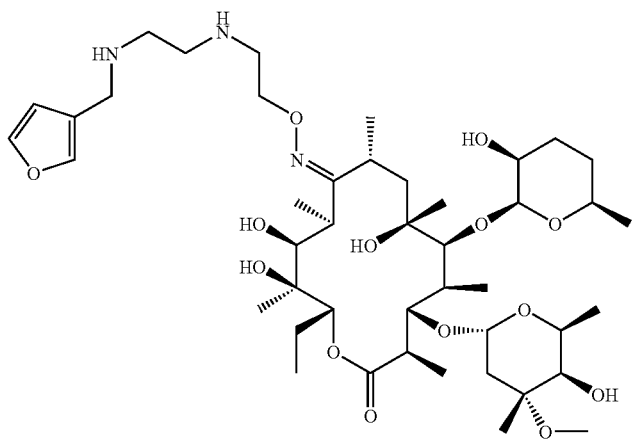 | CDCl$_3$: 7.34 (m, 2H, Fu), 6.37 (m, 1H, Fu); 5.00-5.09 (m, 1H, H$_{13}$); 4.77 (d, 1H, J=4.5, H$_1$''); 4.23 (d, 1H, J=7.6, H$_1$'); 3.92 (s, 1H, H$_{11}$); 3.26 (s, 3H, H$_7$''); 0.80 (t, 3H, J=7.4, H$_{15}$). |

| | | |
|---|---|---|
| Intermediate 24 | 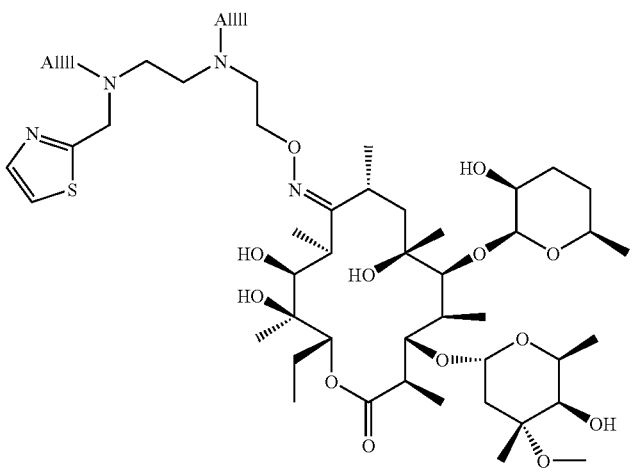 | CDCl$_3$: 7.73 (m, 1H, Th); 7.30 (m, 1H, Th); 5.85-6.1 (m, 2H, CH=C allyl); 3.31 (s, 3H, H$_7$″); 0.85 (t, 3H, J=7.3, H$_{15}$). |
| IntermedIate 37 | 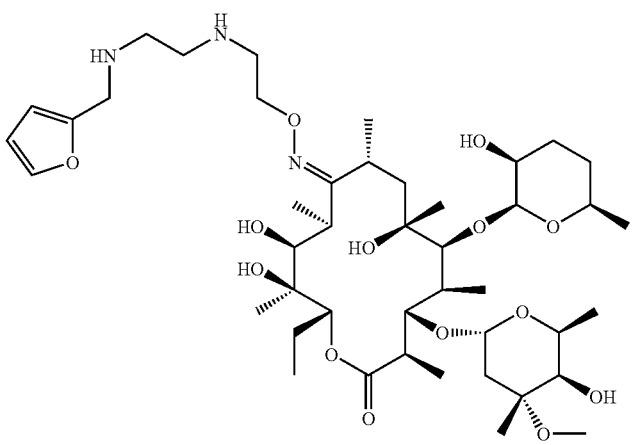 | CDCl$_3$: 7.30, 6.27 and 6.17 (3m, 1H, Fu); 5.03-5.09 (m, 1H, H$_{13}$); 4.80 (d, 1H, J=4.8, H$_1$″); 4.22 (d, 1H, J=7.4, H$_1$′);. 3.81 (s, 1h, H$_{11}$); 3.26 (S, 3H, H$_7$″); 0.80 (t, 3H, J=7.5, H$_{15}$). |
| Intermediate 20 | 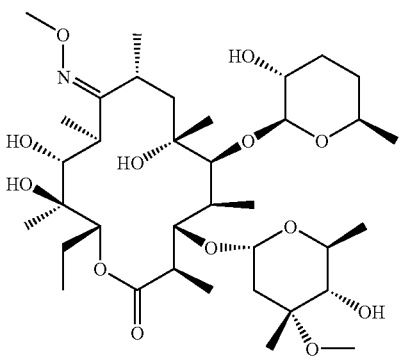 | CDCl$_3$: 5.0-5.2 (m, 1H, H$_{13}$); 4.92 (d, 1H, J=4.5, H$_1$″); 4.31 (d, 1H, J=7.6, H$_1$′); 3.83 (s, 3H, CH$_3$—ON=); 3.31 (s, 3H, H$_7$″); 0.85 (t, 3H, J=7.3, H$_{15}$). |

-continued
Intermediate 38 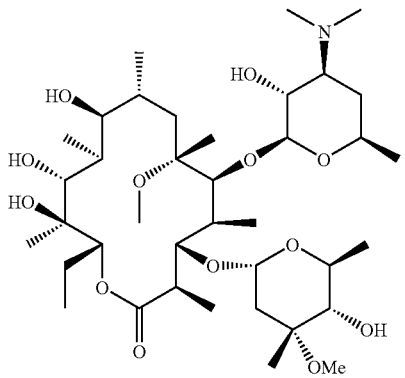
CDCl$_3$: 5.19-5.24 (m, 1H, H$_{13}$), 4.98 (d, 1H, J=4.6, H$_1$"); 4.50 (d, 1H, J=7.1, H$_1$'); 3.38 (s, 3H, cladinose CH$_3$O); 3.35 (s, 3H, H$_7$"); 2.29 (s, 6H, Me$_2$N); 0.85 (t, 3H, J=7.2, H$_{15}$)
Compound 23 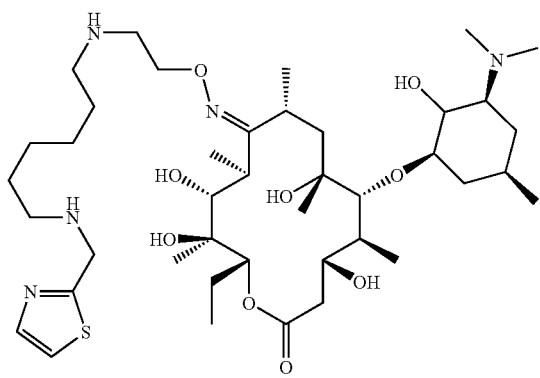
CDCl$_3$: 7.72 (m, 1H, Th); 7.27 (m, 1H, Th); 5.17-5.23 (m, 1H, H$_{13}$); 4.42 (d, 1H, J=7.4, H$_1$'); 4.12 (m, 2H, CH$_2$Th); 3.90 (s, 1H, H$_{11}$); 2.26 (s, 6H, Me$_2$N); 0.84 (t, 3H, J=7.3, H$_{15}$).
Compound 27 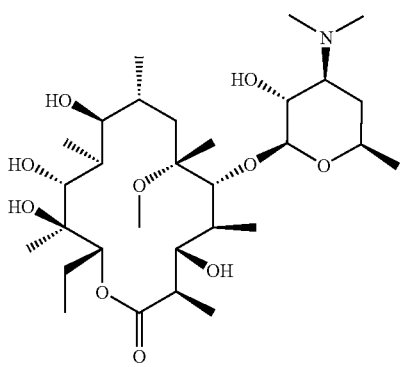
D$_2$O: 5.06-5.11 (m, 1H, H$_{13}$); 3.84 (s, 1H, H$_{11}$); 3.06 (s, 3H, CH$_3$ clarithro); 2.64 and 2.74 (2s, 6H, Me$_2$N); 0.68 (t, 3H, J=7.1, H$_{15}$).
Compound 28 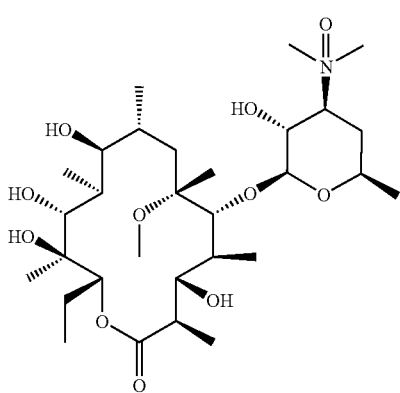
CDCl$_3$: 4.65 (m, 1H, H$_1$'); 3.95 (s, 1H, H$_{11}$); 3.20 and 3.16 (2s, 6H, Me$_2$N[O]); 3.14 (s, 3H, CH$_3$ clarithro); 0.81 (t, 3H, J=7.4, H$_{15}$).

-continued
Compound 22 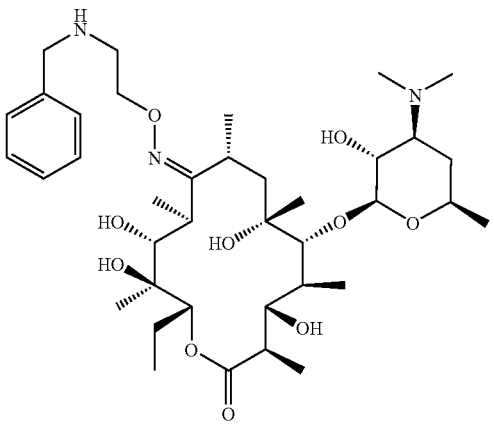 CDCl$_3$: 7.2-7.4 (m, 5H, Ph); 5.2-5.3 (m, 1H, H$_{13}$); 4.29 (d, 1H, J=7.3, H$_1$'); 3.90 (s, 1H, H$_{11}$); 3.74 (m, 2H, CH$_2$Ph); 2.26 (s, 6H, Me$_2$N); 0.86 (t, 3H, J=7.3, H$_{15}$).
Compound 13 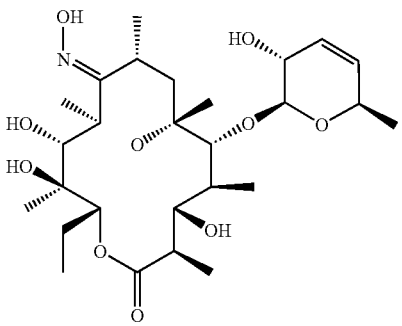 CDCl$_3$: 5.64 (m, 2H, H$_3$' and H$_4$'); 5.17-5.32 (m, 1H, H$_{13}$); 4.56 (d, 1H, J=7.1, H$_1$'); 1.49 (s, 3H, H$_{18}$); 0.84 (t, 3H, J=7.3, H$_{15}$).
Compound 6 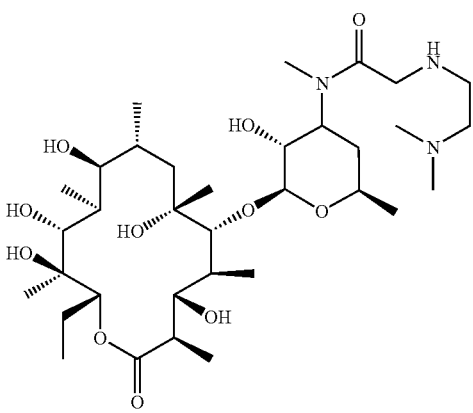 CDCl$_3$: 4.83-4.92 (m, 1H, H$_{13}$); 3.82 (s, 1H, H$_{11}$); 2.77 and 2.72 (2s, 3H, conformers MeN); 2.10 (s, 6H, NMe$_2$); 0.73 (m, 3H, H$_{15}$).
Compound 5 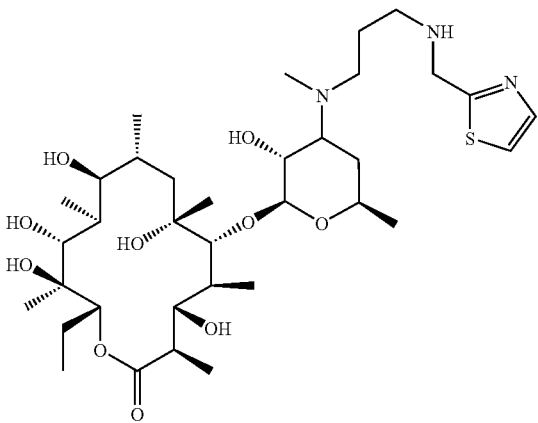 D$_2$O:. 7.66 (m, 1H, Th); 7.47 (m, 1H, Th); 4.91 (m, 1H, H$_{13}$); 4.53 (d, 1H, J=8.0, H$_1$'); 4.12 (m, 2H, CH$_2$Th); 2.52 (s, 3H, MeN); 0.72 (t, 3H, J=7.2, H$_{15}$).

-continued
Compound 7 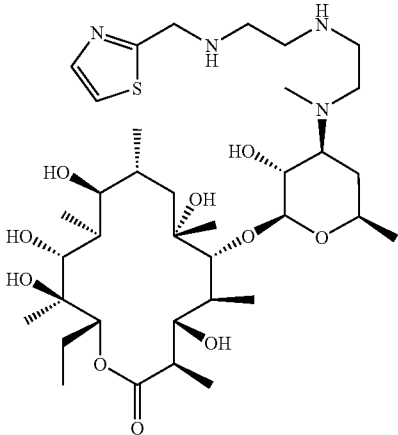
CDCl$_3$: 7.72 (m, 1H, Th); 7.31 (m, 1H, Th); 4.21 (m, 2H, CH$_2$Th); 3.87 (s, 1H, H$_{11}$); 2.37 (s, 3H, MeN); 0.89 (t, 3H, J=7.2, H$_{15}$).
Compound 8 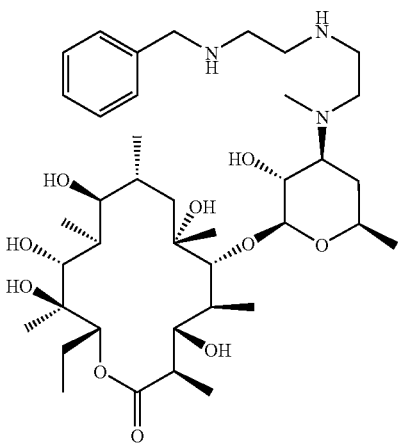
CDCl$_3$: 7.30–7.40 (m, 5H, Ph); 4.40 (d, 1H, J=7.4, H$_1$'); 3.87 (s, 1H, H$_{11}$); 3.80 (m, 2H, CH$_2$Ph); 2.34 (s, 6H, Me$_2$N); 0.92 (t, 3H, J=7.1, H$_{15}$).
Compound 24 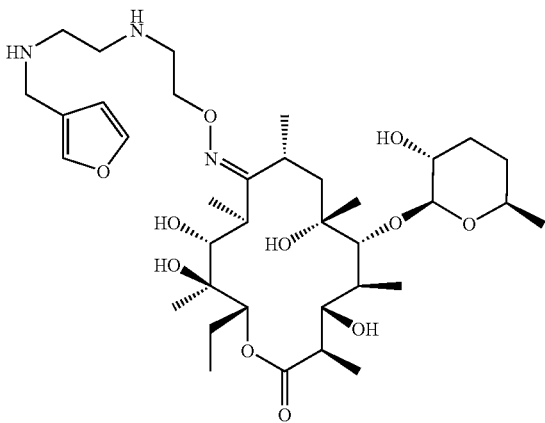
CDCl$_3$: 7.41 (m, 2H, Fu); 6.44 (m, 1H, Fu); 5.14-5.19 (m, 1H, H$_{13}$); 4.29 (d, 1H, J=7.4, H$_1$'); 3.93 (s, 1H, H$_{11}$); 1.39 (s, 3H, H$_{18}$); 0.82 (t, 3H, J=7.3, H$_{15}$).

-continued
Compound 25 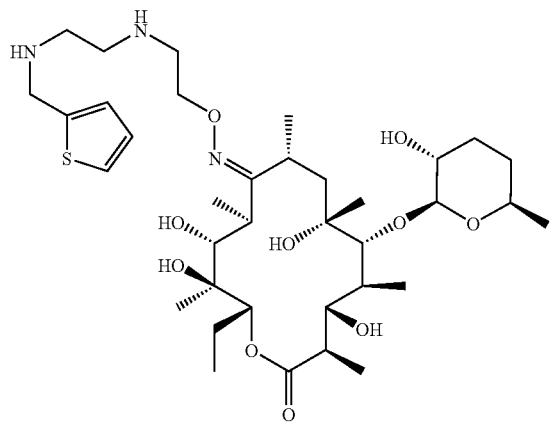
CDCl$_3$: 7.23 (m, 1H, Ti); 6.96 (m, 2H, Ti); 5.16-5.21 (m, 1H, H$_{13}$); 4.30 (d, 1H, J=7.6, H$_1$'); 4.02 (m, 2H, CH$_2$Ti); 3.92 (s, 1H, H$_{11}$); 1.41 (s, 3H, H$_{18}$); 0.82 (t, 3H, J=7.4, H$_{15}$).
Compound 26 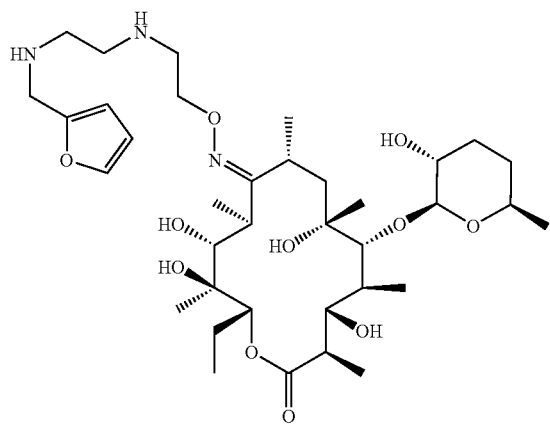
CDCl$_3$: 7.41, 6.34 and 6.24 (3m, 3H, Fu); 5.17-5.22 (m, 1H, H$_{13}$); 4.38 (d, 1H, J=7.7, H$_1$'); 3.93 (s, 1H, H$_{11}$); 1.41 (s, 3H, H$_{18}$); 0.83 (t, 3H, J=7.5, H$_{15}$).
Compound 4 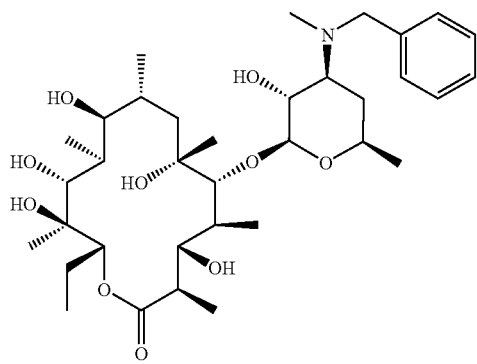
CDCl$_3$: 7.4-7.2 (m, 5H, Ph); 4.55 (m, 1H, H$_{13}$); 4.44 (d, 1H, J=7.7, H$_1$'); 3.89 (s, 1H, H$_{11}$); 2.20 (s, 3H, MeN); 0.93 (t, 3H, J=7.2, H$_{15}$).
Compound 14 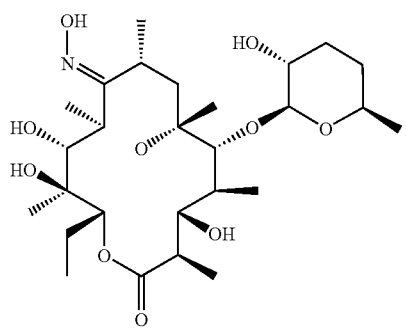
CDCl$_3$: 5.18-5.25 (m, 1H, H$_{13}$); 4.34 (d, 1H, J=7.7, H$_1$'); 3.73 (s, 1H, H$_{11}$); 1.47 (s, 3H, H$_{18}$); 0.86 (t, 3H, J=7.1, H$_{15}$).

-continued
| | | |
|---|---|---|
| Compound 3 | 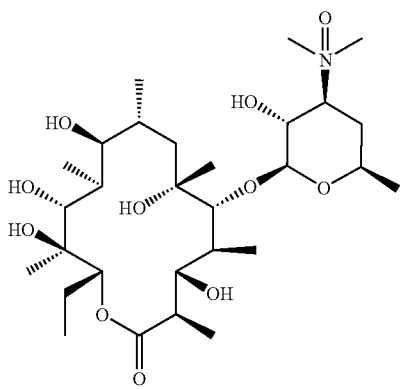 | CDCl$_3$: 4.51 (d, 1H, J=7.2, H$_1$'); 3.19 and 3.16 (2s, 6H, NMe$_2$[O]); 0.88 (t, 3H, J=7.2, H$_{15}$). |
| Intermediate 17 | 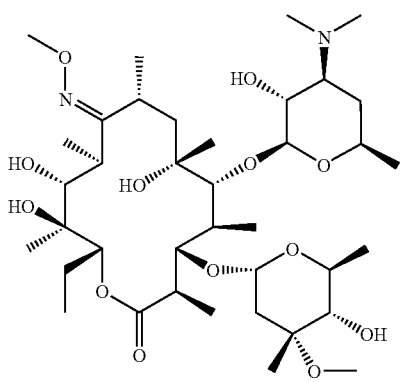 | CDCl$_3$: 5.10-5.15 (m, 1H, H$_{13}$); 4.40 (m, 1H, H$_1$'); 3.84 (s, 3H, CH$_3$—ON=); 3.69 (s, 1H, H$_{11}$); 2.30 (s, 6H, Me$_2$N). |
| Compound 15 | 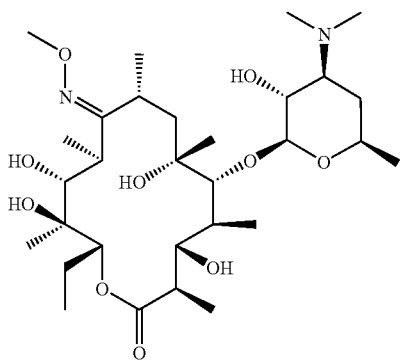 | CDCl$_3$: 5.20-5.31 (m, 1H, H$_{13}$); 4.41 (m, 1H, H$_1$'); 3.85 (s, 3H, CH$_3$—ON=); 2.27 (s, 6H, NMe$_2$); 1.42 (s, 3H, H$_{18}$); 0.86 (t, 3H, H$_{15}$). |
| Intermediate 18 | 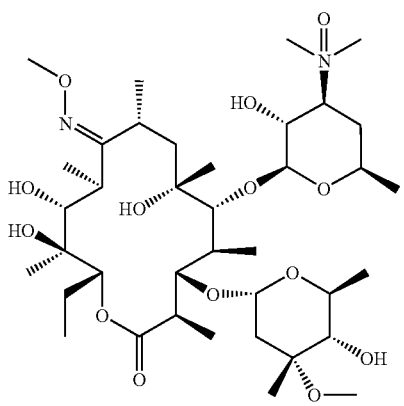 | CDCl$_3$: 5.00-5.20 (m, 1H, H$_{13}$); 4.54 (d, 1H, J=7.0, H$_1$'); 3.83 (s, 3H, CH$_3$—ON=); 3.36 (s, 3H, H$_7$''); 3.21 (s, 6H, Me$_2$N[O]); 1.46 (s, 3H, H$_{18}$); 0.85 (t, 3H, J=7.4, H$_{15}$). |

| | | |
|---|---|---|
| Compound 16 | 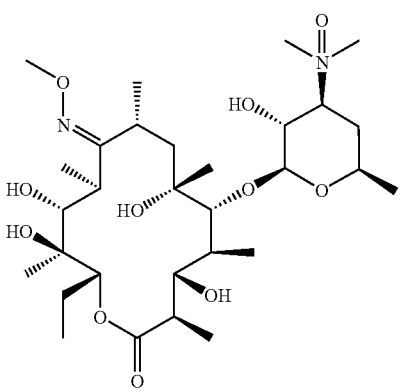 | CDCl$_3$: 5.28-5.20 (m, 1H, H$_{13}$); 4.54 (d, 1H, J=7.0, H$_1$'); 3.85 (s, 1H, H$_{11}$); 3.15 and 3.20 (2s, 6H, Me$_2$N[O]) 1.41 (s, 3H, H$_{18}$); 0.84 (t, 3H, J=7.5, H$_{15}$). |
| Intermediate 19 | 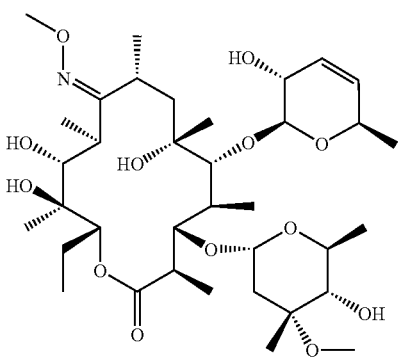 | CDCl$_3$: 5.7 (m, 2H, H$_3$' and H$_4$'); 5.12-5.18 (m, 1H, H$_{13}$); 4.92 (d, 1H, J=4.2, H$_1$'); 4.51 (d, 1H, J=6.5, H$_1$'); 3.85 (s, 3H, CH$_3$—ON); 3.30 (s, 3H, H$_7$''); 0.87 (t, 3H, J=7.2, H$_{15}$). |
| Compound 17 | 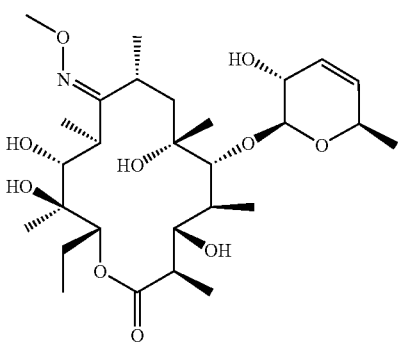 | CDCl$_3$: 5.66 (m, 2H, H$_3$' and H$_4$'); 5.22-5.29 (m, 1H, H$_{13}$); 4.56 (m, 1H, H$_1$'); 3.87 (s, 3H, CH$_3$—ON); 3.70 (s, 1H, H$_{11}$); 1.43 (s, 3H, H$_{18}$); 0.87 (t, 3H, J=7.3, H$_{15}$). |
| Compound 18 | 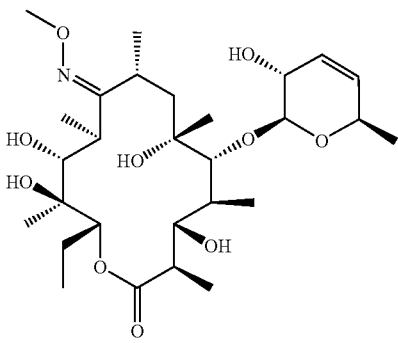 | CDCl$_3$: 5.22-5.29 (m, 1H, H$_{13}$); 4.35 (d, 1H, J=7.6, H$_1$'); 3.86 (s, 3H, CH$_3$—ON=); 3.69 (s, 1H, H$_{11}$); 1.41 (s, 3H, H$_{18}$); 0.86 (t, 3H, J=7.4, H$_{15}$). |

-continued
Intermediate 16
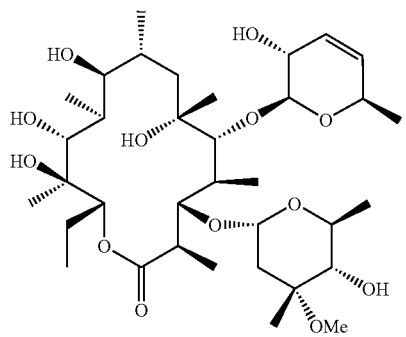
CDCl₃: 5.5 (m, 2H, $H_3'$ and $H_4'$); 5.00-5.04 (m, 1H, $H_{13}$); 3.81 (s, 3H, $H_{11}$); 0.91 (t, 3H, J=7.4, $H_{15}$).
Compound 1
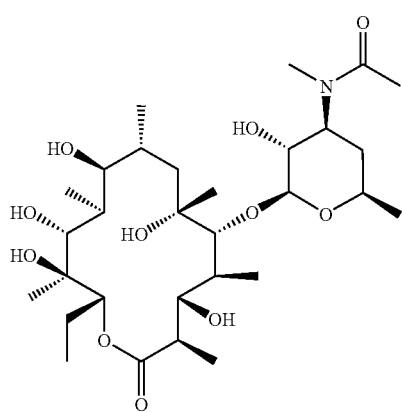
CDCl₃: 2.96 and 2.86 (2s, 3H, conformers MeN); 2.21 and 2.17 (2s, 3H, CH₃CO); 0.93 (t, 3H, J=7.4, $H_{15}$).
Compound 11
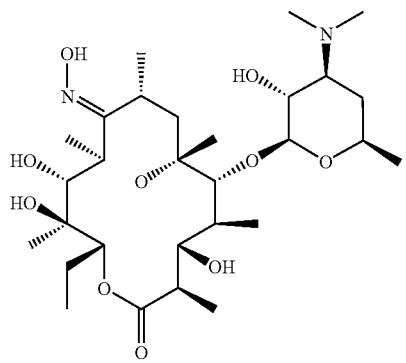
CDCl₃: 5.17-5.24 (m, 1H, $H_{13}$); 4.40 (d, 1H, J=7.4, $H_1'$); 3.72 (s, 1H, $H_{11}$); 2.27 (s, 6H, NMe₂); 0.85 (t, 3H, J=7.4; $H_{15}$).
Compound 12
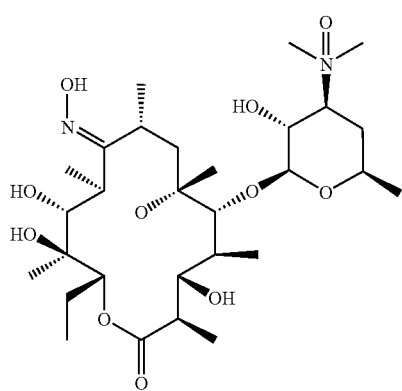
HDMSO_d6: 5.14-5.19 (m, 1H, $H_{13}$); 4.48 (d, 1H, J=7.2, $H_1'$); 3.90 (s, 1H, $H_{11}$); 3.04 and 3.00 (2s, 6H, NMe₂[O]); 1.23 (s, 3H, $H_{18}$); 0.73 (1, 3H, J=7.1; $H_{15}$).

-continued
Compound 2
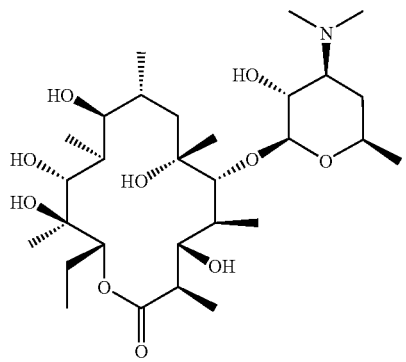
CDCl$_3$: 4.50 (m, 1H, H$_{13}$); 4.34 (d, 1H, J=7.4, H$_1$'); 3.89 (s, 1H, H$_{11}$); 2.29 (s, 6H, Me$_2$N); 0.93 (t, 3H, J=7.4, H$_{15}$).
Intermediate 10
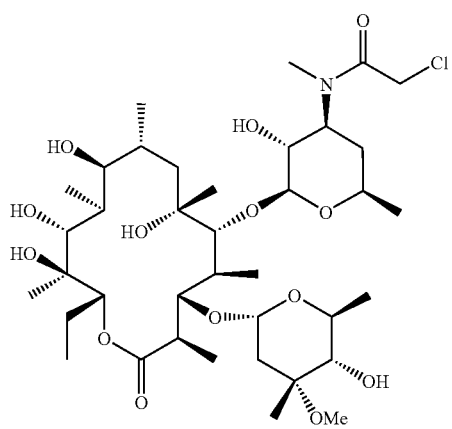
CDCl$_3$: 3.33 and 3.31 (2s, 3H, H$_7$''); 3.03 and 2.88 (2s, 3H, MeN); 0.92 (m, 3H, H$_{15}$).
Intermediate 11
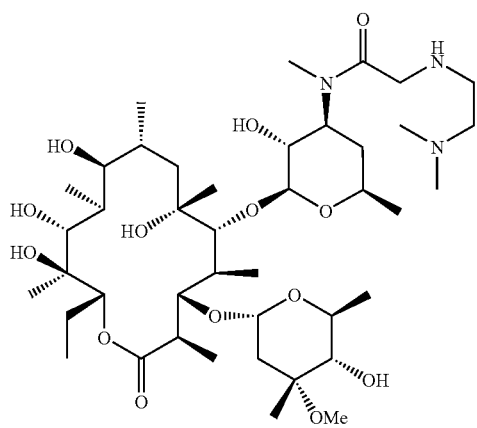
DMSO_d6: 4.95 (m, 2H, C[O]CH$_2$N); 4.83 (m, 1H, H$_1$'); 2.09 (s, 6H, Me$_2$N); 0.77 (m, 3H, H$_{15}$)
Intermediate 1
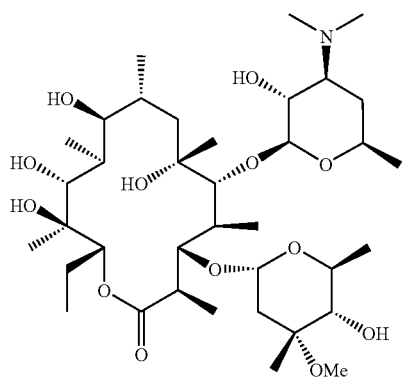
CDCl$_3$: 4.98 (d, 1H, J=4.1, H$_1$''); 4.91 (m, 1H, H$_{13}$); 4.54 (d, 1H, J=7.2, H$_1$'); 3.75 (s, 1H, H$_{11}$); 3.32 (s, 3H, H$_7$''); 2.30 (s, 6H, Me$_2$N); 0.89 (t, 3H, J=7.4, H$_{15}$).

-continued
| | | |
|---|---|---|
| Intermediate 2 | 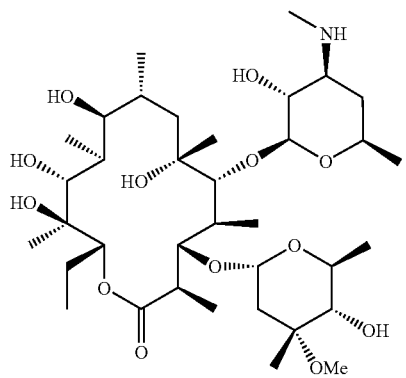 | CDCl$_3$: 5.02 (m, 1H, H$_{13}$), 4.78.(d, 1H, J=4.0, H$_1$"); 4.49 (d, 1H, J=7.4, H$_1$'); 3.79 (s, 1H, H$_{11}$); 3.29 (s, 3H, H$_7$"); 2.44 (s, 3H, MeN); 0.91 (t, 3H, J=7.6, H$_{15}$). |
| Intermediate 3 | 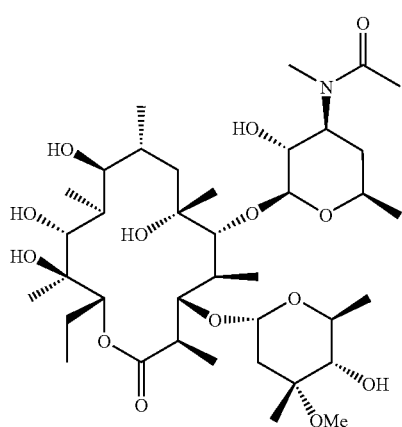 | CDCl$_3$: 3.33 and 3.29 (2s, 3H, H$_7$"); 2.93 and 2.88 (2s, 3H, MeN); 2.18 and 2.14 (2s, 3H, N[CO]CH$_3$); 0.91 (t, 3H, J=7.1, H$_{15}$). |
| Intermediate 36 | 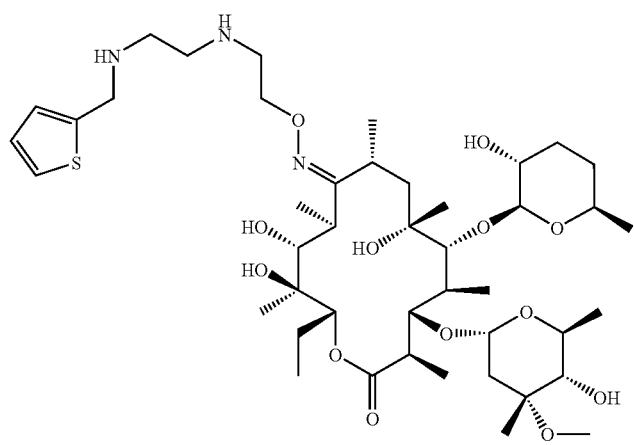 | CDCl$_3$: 7.17 (m, 1H, Thio), 6.96 (m, 2H, Thio); 5.06 (m, 1H, H$_{13}$); 4.81 (d, 1H, J=4.2, H$_1$"); 4.24 (d, 1H, J=7.5, H$_1$'); 3.90 (s, 1H, H$_{11}$); 3.26 (s, 3H, H$_7$"), 0.81 (t, 3H, J=7.4, H$_{15}$). |
| IntermedIate 7 | 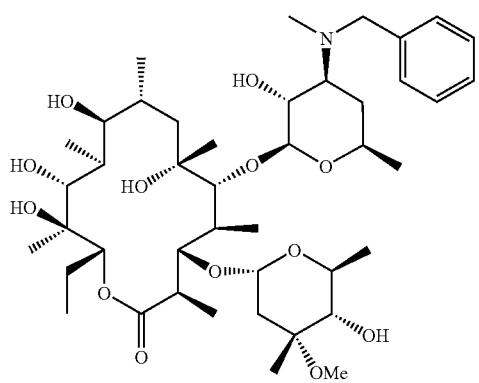 | CDCl$_3$: 7.25-7.40 (m, 5H, Ph); 5.02 (d, 1H, J=4.3, H$_1$"); 4.87 (m, 1H, H$_{13}$); 4.55 (d, 1H, J=7.2, H$_1$'); 3.12 (s, 3H, H$_7$"); 2.28 (s, 3H, MeN); 0.90 (t, 3H, J=7.5, H$_{15}$) |

-continued
| | | |
|---|---|---|
| Intermediate 8 | 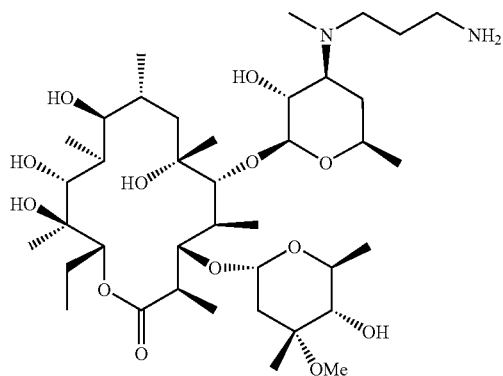 | D$_2$O: 4.88 (d, 1H, J=4.3, H$_1$"); 4.78 (m, 1H, H$_{13}$); 4.55 (d, 1H, J=7.3, H$_1$'); 3.11 (s, 3H, H$_7$"); 2.16 (s, 3H, MeN); 0.74 (t, 3H, J=7.3, H$_{15}$) |
| Intermediate 9 | 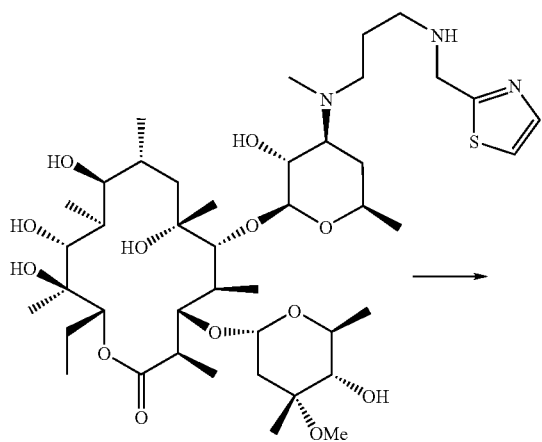 | CDCl$_3$: 7.73 (m, 1H, Th); 7.27 (m, 1H, Th); 5.01 (d, 1H, J=4.2, H$_1$"); 4.90 (m, 1H, H$_{13}$); 4.55 (d, 1H, J=7.1, H$_1$'); 4.12 (m, 2H, CH$_2$Th); 3.33 (s, 3H, H$_7$"); 2.28 (s, 3H, MeN); 0.90 (t, 3H, J=7.4, H$_{15}$). |
| Intermediate 12 | 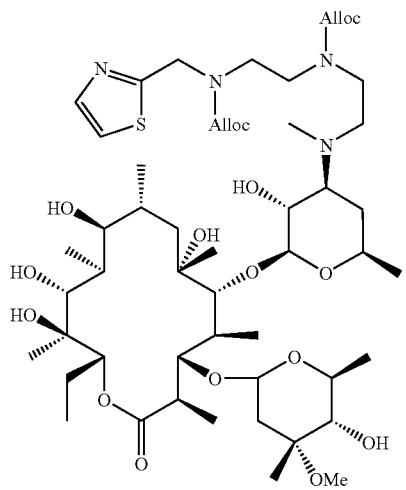 | CDCl$_3$: 7.10 (m, 1H, Th); 7.28 (m, 1H, Th); 5.8-6.1 (m, 2H, =CH allyl); 5.02 (d, 1H, J=4.1, H$_1$'); 4.90 (m, 1H, H$_{13}$); 3.77 (s, 1H, H$_{11}$); 3.30 (s, 3H, H$_7$"); 2.31 (s, 3H, MeN); 0.89 (t, 3H, J=7.2, H$_{15}$). |

| | | |
|---|---|---|
| Intermediate 13 | 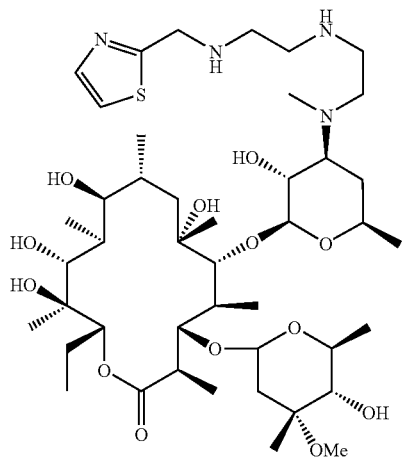 | CDCl$_3$: 7.70 (m, 1H, Th); 7.26 (m, 1H, Th); 4.98 (d, 1H, J=4.2, H$_1$"); 4.90 (m, 1H, H$_{13}$); 4.53 (d, 1H, J=7.1, H$_1$'); 4.13 (m, 2H, CH$_2$Th);. 3.73 (s, 1H, H$_{11}$); 3.32 (s, 3H, H$_7$"); 2.29 (s, 3H, MeN); 0.88 (t, 3H, J=7.1, H$_{15}$). |
| Intermediate 14 | 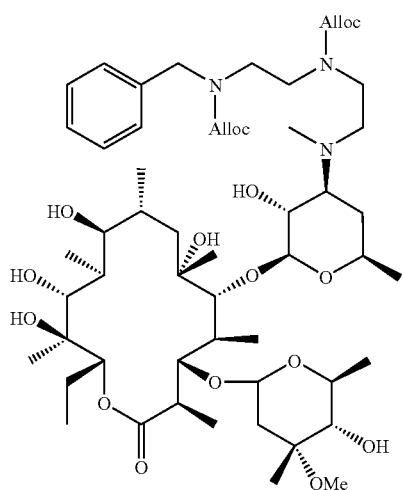 | CDCl$_3$: 7.20-7.32 (m, 5H, Ph); 5.8-6.1 (m, 2H, =CH allyl); 5.00 (d, 1H, J=4.0, H$_1$"); 4.90 (m, 1H, H$_{13}$); 3.75 (s, 1H, H$_{11}$); 3.32 (s, 3H, H$_7$"); 2.29 (s, 3H, MeN), 0.90 (t, 3H, J=7.5, H$_{15}$). |
| Intermediate 15 | 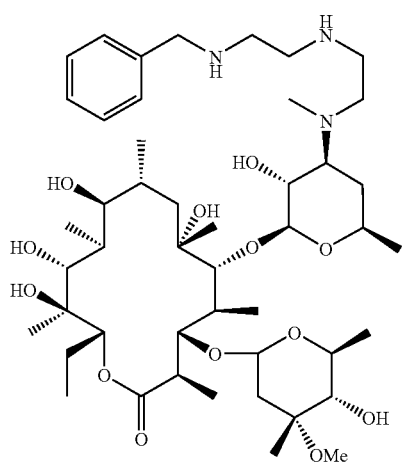 | CDCl$_3$: 7.25-7.35 (m, 5H, Ph); 5.00 (d, 1H, J=3.9, H$_1$"); 4.89 (m, 1H, H$_{13}$); 4.55 (d, 1H, J=7.2, H$_1$'); 3.82 (m, 2H, CH$_2$Ph); 3.77 (s, 1H, H$_{11}$); 3.34 (s, 3H, H$_7$"); 2.30 (s, 3H MeN); 0.91 (t, 3H, J=7.5, H$_{15}$). |

| | | |
|---|---|---|
| Intermediate 5 | 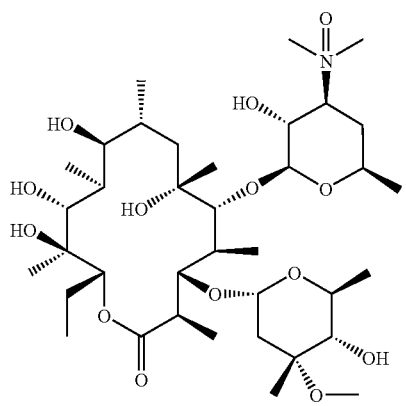 | CDCl$_3$: 5.03 (d, 1H, J=3.9, H$_1$"); 4.83 (m, 1H, H$_{13}$); 4.69 (d, 1H, J=7.0, H$_1$'); 3.76 (s, 1H, H$_{11}$); 3.41 (s, 6H, Me$_2$N[O]); 3.23 (s, 3H, H$_7$"); 0.91 (t, 3H, J=7.5, H$_{15}$). |
| Compound 9 | 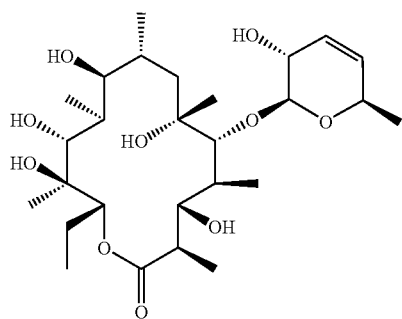 | CDCl$_3$: 5.69 (m, 2H, H$_3$' and H$_4$'); 4.59 (m, 1H, H$_{13}$); 4.51 (d, 1H, J=6.9, H$_1$'); 3.85 (s, 3H, H$_{11}$); 0.92 (t, 3H, J=7.4, H$_{15}$). |
| Compound 10 | 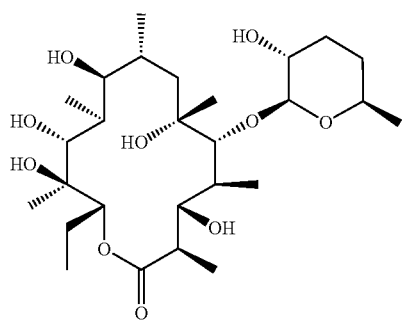 | CDCl$_3$: 4.58 (m, 1H, H$_{13}$); 4.36 (d, 1H, J=7.6, H$_1$'); 3.86 (s, 3H, H$_{11}$); 1.35 (s, 3H, H$_{18}$); 0.92 (t, 3H, J=7.4, H$_{15}$). |
| Intermediate 30 | 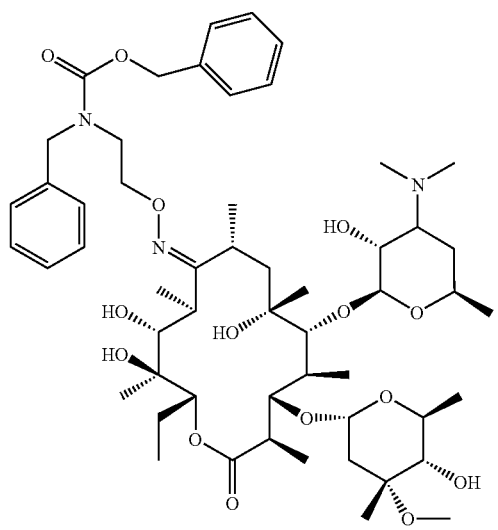 | CDCl$_3$: 7.1-7.4 (m, 10H, 2Ph); 5.2 (m, 4H, 2CH$_2$Ph); 4.8 (m, 1H, H$_1$"); 4.4 (m, 1H, H$_1$'); 3.31 (s, 3H, H$_7$"); 2.29 (s, 6H, Me$_2$N); 0.82 (m, 3H, H$_{15}$). |

-continued
| Intermediate 31 | 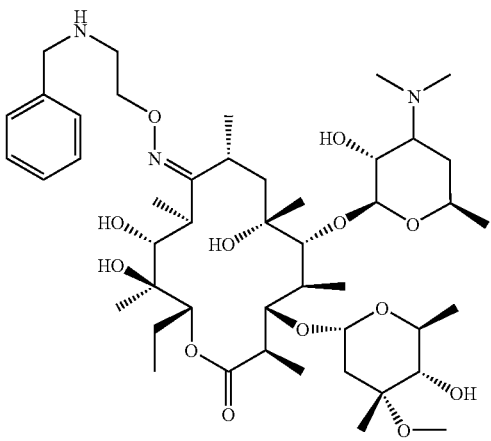 | CDCl₃: 7.05-7.38 (m, 5H, Ph); 5.10 (m, 1H, H$_{13}$); 4.8 (m, 1H, H$_1$"); 4.40 (m, 1H, H$_1$'); 3.28 (s, 3H, H$_7$"); 2.35 (s, 6H, Me₂N); 0.8 (m, 3H, H$_{15}$). |
| --- | --- | --- |
| Intermediate 33 | 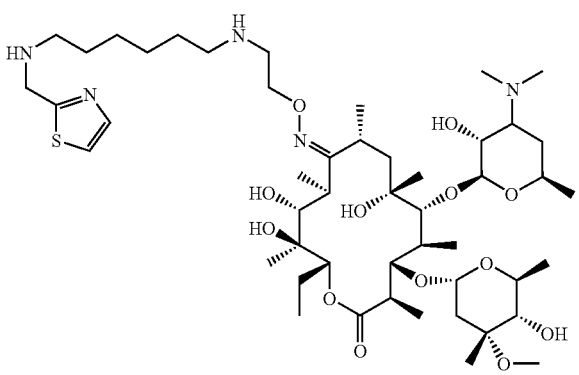 | CDCl₃: 7.65 (m, 1H, Th); 7.24 (m, 1H, Th); 5.05 (m, 1H, H$_{13}$); 4.78 (m, 1H, H$_1$'); 4.35 (m, 1H, H$_1$'); 3.82 (s, 1H, H$_{11}$); 3.23 (s, 3H, H$_7$"); 2.20 (s, 6H, Me₂N); 0.80 (m, 3H, H$_{15}$). |
| Intermediate 39 | 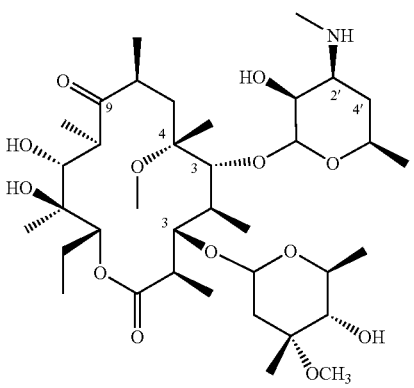 | CDCl₃: 5.05 (m, 1H, H$_{13}$); 4.92 (d, 2H, J=4.5, H$_1$"); 4.41 (d, 2H, J=7.5, H$_1$'); 3.98 (s, 1H, H$_{11}$); 3.32 (s, 3H, H$_7$"); 3.03 (s, 3H, CH$_3$ clarithro); 2.41 (s, 3H, MeN); 0.84 (t, 3H, J=7.4, H$_{15}$) |
| Intermediate 40 | 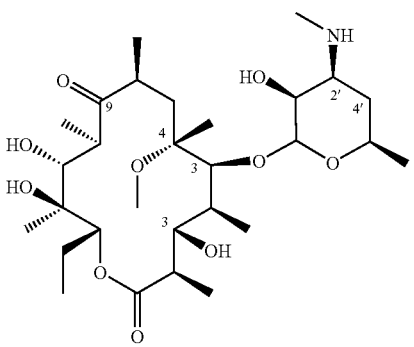 | CDCl₃: 5.17 (m, 1H, H$_{13}$); 4.41 (d, 2H, J=8.1, H$_1$'); 2.96 (s, 3H, CH$_3$ clarithro); 2.42 (s, 3H, MeN); 0.83 (t, 3H, J=7.5, H$_{15}$) |

-continued
| | | |
|---|---|---|
| Intermediate 41 | 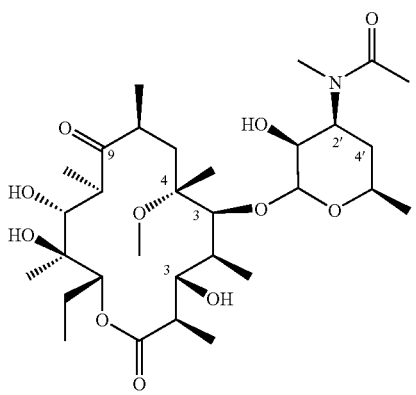 | CDCl$_3$: 4.50 (d, 2H, J=7.4, H$_1$'); 3.93 (s, 1H, H$_{11}$); 2.96 (s, 3H, CH$_3$ clarithro); 2.91 (s, 3H, MeN); 2.15 and 2.12 (2s, 3H, conformers CH$_3$CO); 0.83 (t, 3H, J=7.4, H$_{15}$) |
| Compound 29 | 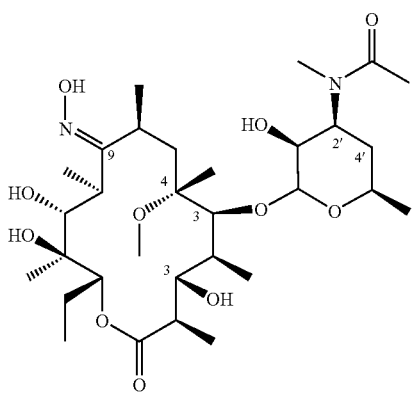 | CDCl$_3$: 5.19 (m, 1H, H$_{13}$); 4.48 (m, H, H$_1$'); 3.80 (s, 1H, H$_{11}$); 3.00 (s, 3H, CH$_3$ clarithro), 2.89 (s, 3H, MeN); 2.18 and 2.12 (2s, 3H, conformers CH$_3$CON); 0.92 (m, 3H, H$_{15}$) |
| Intermediate 4 | 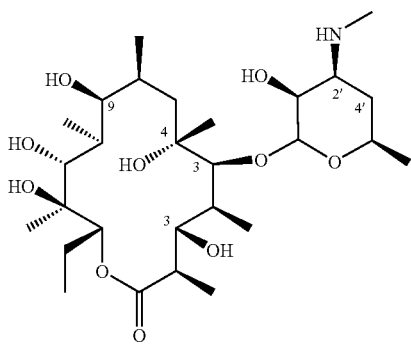 | HPLC: Rt 3.01 min |
| Compound 30 | 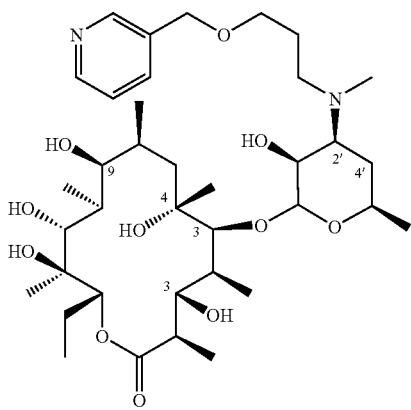 | CDCl$_3$: 8.62, 8.56, 7.75 and 7.30 (4m, 4H, Py); 4.74 (s, 2H, CH$_2$Py); 3.89 (s, 1H, H$_{11}$): 2.97 (s, 3H, CH$_3$N); 0.87 (m, 3H, H$_{15}$) |

Intermediate 6

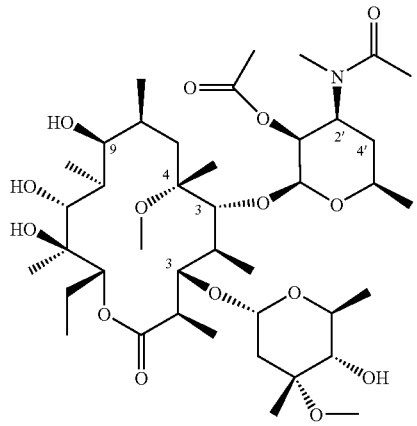

HPLC: Rt 6.17 min

Key to table: Alloc = allyloxycarbonyl

EXAMPLE 1

Preparation of Intermediate 1

A solution of NaBH$_4$ (11.3 g, 300 mmol) in H$_2$O (75 ml) was added dropwise (over more than 20 minutes) to a solution of erythromycin (100 g, 136.3 mmol) in THF (1.5 L) maintained at 0° C. The reaction mixture was stirred for 1 hour at 0° C. and for 3 hours at room temperature. Evaporation of the THF under vacuum gave a crude product, which was dissolved in ethyl acetate (0.5 L) and citric acid (1 L of an aqueous 5% solution). The aqueous phase was extracted, washed with ethyl acetate (3×0.5 L) and neutralized with K$_2$CO$_3$. Extraction with ethyl acetate (3×1 L) gave an organic phase, which was dried over sodium sulphate, filtered and evaporated under vacuum to give intermediate 1 (72.1 g, 72% yield, 89.6% d.e.) as a white solid.
[M+1]$^+$ 736

EXAMPLE 2

Preparation of Intermediate 2

A solution of intermediate 1 (10.3 g, 14 mmol) in methanol (120 ml) was maintained under a stream of nitrogen and sodium acetate (5.7 g, 70 mmol) and iodine (4.28 g, 16.9 mmol) were sequentially added thereto. The reaction mixture was kept stirring and irradiated with a 400 watt UV lamp for 6 hours, while maintaining the temperature between 20-30° C. with an ice bath. The methanol was evaporated off under vacuum and the residue was taken up in ethyl acetate and extracted with 5% sodium metabisulphate. The combined aqueous phase was treated with 10% NaOH solution to alkaline pH and extracted with ethyl acetate (4×0.5 L). After drying with sodium sulphate, the organic phase was filtered and evaporated under vacuum to give 10 g of a white solid crude product, which was dissolved in ethyl acetate (40 ml at 50° C.) and crystallized to give intermediate 2 (5.3 g, 53% yield) as a white solid.
[M+1]$^+$ 722

EXAMPLE 3

Preparation of Intermediate 3

A solution of acetic anhydride (31 µl, 0.33 mmol) dissolved in dioxane (1 ml) was added to a solution of intermediate 2 (200 mg, 0.277 mmol) and K$_2$CO$_3$ (76 mg, 0.554 mmol) in dioxane (4 ml) and water (5 ml). After 3 hours, methanol was added and the solution was evaporated under vacuum. The crude solid was dissolved in ethyl acetate (20 ml) and washed with 5% citric acid (2×10 ml) and 10% K$_2$CO$_3$ (2×10 ml). The organic phase was dried over sodium sulphate and filtered, and the solvent was evaporated off to give intermediate 3 (130 mg, 62% yield) as a white solid.
[M−1]$^-$ 763

EXAMPLE 4

Preparation of Compound 1 (1$^{st}$ Synthesis Route)

Concentrated HCl (0.5 ml) was added dropwise to a solution of intermediate 3 (470 mg, 0.618 mmol) in methanol (50 ml) and the reaction mixture was stirred for 1 hour. After neutralizing with concentrated NH$_3$, the solution was evaporated, dissolved in CH$_2$Cl$_2$, the inorganic salts were filtered off and solvent was evaporated off under vacuum. Purification by Biotage chromatography (40M silica cartridge, 30/1 CH$_2$Cl$_2$/MeOH) gave compound 1 (329 mg, 90% yield) as a white solid.
[M−1]$^-$ 604

EXAMPLE 5

Preparation of Intermediate 4

Concentrated HCl (5 µl) was added to a heterogeneous solution of intermediate 2 (1 g, 1.38 mmol) in H$_2$O (10 ml) and the reaction mixture was stirred vigorously for 5 days. 1 ml of concentrated NH$_3$ (pH>8) was added to the solution, followed by extraction with ethyl acetate (3×10 ml). The combined organic phase was washed with NaCl solution, (10 ml, 20%), dried over sodium sulphate, filtered and evaporated under vacuum to give intermediate 4 (0.73 g, 90% yield) as a white solid.
[M+1]$^+$ 565

HPLC-MS: Zorbax SB-C18, 2.1×50 mm, 3.5 mm column; column temperature 45° C.; mobile phase A 0.1% formic acid in $H_2O$, B 0.1% formic acid in acetonitrile; gradient 0 min. 5% B, 8 min. 95% B; flow rate 1 ml/min.; injection volume 2 μl; sample concentration 0.5-1 mg/ml; mass spectrometer detector equipped with an electron spray ionization source, positive ionization; retention time 3.01 min. which corresponds to 3.22 for compound 2; total run time 8 min. plus 2 min. of reequilibration.

EXAMPLE 6

Preparation of Compound 1 ($2^{nd}$ Synthesis Route)

Compound 1 was prepared from intermediate 4 (0.73 g, 0.97 mmol) and acetic anhydride (91 ml, 0.97 mmol) according to the procedure described for obtaining intermediate 3. After 3 hours, the reaction mixture was diluted with methanol and evaporated under vacuum. The solid crude product was dissolved in aqueous 5% citric acid solution and extracted with ethyl acetate. The combined organic phases were washed with aqueous 20% NaCl solution, dried over sodium sulphate, filtered and evaporated under vacuum to give compound 1 (0.56 g, 95% yield) as a white solid.
$[M-1]^-$ 604

EXAMPLE 7

Preparation of Compound 2

Compound 2 was prepared from intermediate 1 (322 mg, 0.438 mmol) according to the procedure described for obtaining compound 1. After neutralizing with concentrated $NH_3$, the solution was evaporated. The crude product was dissolved in 1 N HCl and washed with $CH_2Cl_2$ (3×10 ml) and was added to the aqueous $K_2CO_3$ phase to alkaline pH. Extraction with ethyl acetate gave an organic phase, which was dried over sodium sulphate and filtered to give compound 2 (225 mg, 89% yield) as a white solid.
$[M+1]^+$ 578

EXAMPLE 8

Preparation of Intermediate 5 meta-Chloroperbenzoic acid (1.35 g, 6.06 mmol) was added portionwise to a solution of intermediate 1 (4.4 g, 6 mmol) in chloroform (250 ml) and the reaction mixture was diluted with 5% sodium bicarbonate solution to basic pH. The organic phase was separated out and the aqueous phase was washed with $CH_2Cl_2$ (3×50 ml). The combined organic solution was washed with 20% NaCl solution, dried over sodium sulphate, filtered and evaporated to give a yellow solid. Purification by Biotage chromatography (40M silica cartridge, 20/1/0.1 $CH_2Cl_2$/MeOH/$NH_3$ eluent) gave white crystals of intermediated 5 (1.3 g, 70% yield).
$[M+1]^+$ 753

EXAMPLE 9

Preparation of Compound 3

Compound 3 was prepared from intermediate 5 (2.07 g, 0.275 mmol) according to the procedures described for compound 1. Purification by Biotage chromatography (40M silica cartridge, 16/1/0.1 $CH_2Cl_2$/MeOH/$NH_3$ eluent) gave compound 3 (1.44 g, 88% yield) as a white solid.
$[M+1]^+$ 595

EXAMPLE 10

Preparation of Intermediate 6

Acetic anhydride (26 ml, 276 mmol) was added dropwise to a solution of intermediate 5 (70 g, 95 mmol) in $CH_2Cl_2$ (0.5 L) and the reaction mixture was stirred for 1 day. Although a small amount of unreacted starting material was still present, the reaction was neutralized by adding 5% $NaHCO_3$ solution (1 L) and stirred for a further 10 minutes. The solution was diluted with $CH_2Cl_2$ (0.5 L); the organic phase was separated out and washed with 10% $K_2CO_3$ solution (3×0.5 L), 5% citric acid solution (3×0.5 L) and 20% NaCl solution (0.3 L). The solution was evaporated to give a white solid crude product (50 g), which, although containing 40% unreacted material, was used directly for the following synthesis step.
$[M-1]^-$ 805

HPLC-MS: Zorbax SB-C18, 2.1×50 mm, 3.5 mm column; column temperature 45° C.; mobile phase A 0.1% formic acid in $H_2O$, B 0.1% formic acid in acetonitrile; gradient 0 min. 5% B, 8 min. 95% B; flow rate 1 ml/min.; injection volume 2 μl; sample concentration 0.5-1 mg/ml; mass spectrometer detector equipped with an electron spray ionization source, negative ionization; retention time 6.17 min., which corresponds to 3.22 for compound 2; total run time 8 min. plus 2 min. of reequilibration.

EXAMPLE 11

Preparation of Intermediate 3 ($2^{nd}$ Synthesis Route)

$K_2CO_3$ (34 g. 250 mmol) was added to a solution of intermediate 6 (50 g crude mixture) in methanol (500 ml) and water (160 ml), and the mixture was stirred at 60° C. for 8 hours. After cooling to 0° C. on an ice-water bath, HCl (120 ml of a 2N solution) was added to pH, 7. The solution was evaporated under vacuum to remove, the methanol and extracted with $CH_2Cl_2$ (4×0.5 L). The combined organic phase was dried over sodium sulphate, filtered and evaporated to give a solid white crude product (36 g). Purification by flash chromatography (silica, 25/1 $CH_2Cl_2$/MeOH) gave intermediate 3 (14 g, 20% overall yield for the last 2 steps).
$[M-1]^-$ 763

EXAMPLE 12

Preparation of Intermediate 7

4 Å molecular sieves (0.2 g), benzaldehyde (0.060 ml, 0.56 mmol), acetic acid (0.04 ml, 0.7 mmol) and tetramethylammonium triacetoxy borohydride (306 g, 1.16 mmol) were sequentially added to a solution of intermediate 2 (336 mg, 0.465 mmol) in dichloroethane (15 ml). The reaction mixture was stirred for 1 day, filtered through a pad of Celite while washing with $CH_2Cl_2$ (20 ml), and was diluted with 5% $NaHCO_3$ solution (10 ml) and 20% NaCl solution (10 ml). The organic layer was separated out and the aqueous phase was extracted with $CH_2Cl_2$ (3×20 ml). The combined organic phase was dried over sodium sulphate, filtered and evaporated under vacuum. Purification by Biotage chromatography (12M silica cartridge, 30/1/0.1 $CH_2Cl_2$/MeOH/$NH_3$ eluent) gave intermediate 7 (250 mg, 67% yield)
$[M+1]^+$ 813.

EXAMPLE 13

Preparation of Compound 4

Compound 4 was prepared from intermediate 2 (200 mg, 0.868 mmol) according to the procedures described for compound 1. Purification by Biotage chromatography (12M silica cartridge, 30/1/0.1 $CH_2Cl_2$/MeOH/$NH_3$ eluent) gave compound 4 (92 mg, 57% yield).
$[M+1]^+$ 654

EXAMPLE 14

Preparation of Intermediate 8

A solution of intermediate 2 (530 mg, 0.734 mmol) in acrylonitrile (10 ml) was refluxed for 6 hours. The excess acrylonitrile was evaporated off under vacuum to give the crude product of the N-methyl-N-[2-(cyano)ethyl] derivative, which was dissolved in a 1.5 M solution of $NH_3$ in methanol (10 ml), transferred into a high-pressure flask and, after adding the rhodium catalyst (5% on $Al_2O_3$, 100 mg) and 3 hydrogenation cycles, it was stirred for 4 hours under a hydrogen atmosphere of 50 psi. Purification by Biotage chromatography (12M silica cartridge, 90/10/1 $CH_2Cl_2$/MeOH/$NH_3$ eluent) gave intermediate 8 (310 mg, 55% yield over the two steps).
$[M+1]^+$ 780

EXAMPLE 15

Preparation of Intermediate 9

3 Å molecular sieves (1 g) and a solution of 2-thiazolecarboxaldehyde (45 mg, 0.4 mmol) in ethanol (1 ml) were sequentially added to a solution of intermediate 8 (306 mg, 0.397 mmol) in absolute ethanol (5 ml). After 6 hours, the reaction mixture was filtered through a silica pad while washing with ethanol (5 ml) and transferred into a high-pressure flask; to which were added acetic acid (0.5 ml) and 10% Pd/C (150 mg). Using Parr apparatus, the solution was stirred under a hydrogen atmosphere at 50 psi overnight. Filtration through a pad of Celite, evaporation under vacuum and purification by Biotage chromatography (12M silica cartridge, 20/1/0.1 $CH_2Cl_2$/MeOH/$NH_3$ eluent) gave intermediate 9 (140 g, 41% yield) as a white solid.
$[M+1]^+$ 877

EXAMPLE 16

Preparation of Compound 5

Compound 5 was prepared from intermediate 9 (70 mg, 0.08 mmol) according to the procedures described for compound 1. The reaction mixture was diluted with distilled water (20 ml), the solvent was evaporated off, and the aqueous phase was washed with $CH_2Cl_2$ (3×10 ml), concentrated aqueous ammonia was added to pH>7, and the mixture was extracted with $CH_2Cl_2$ (3×10 ml). The combined organic phase was dried over sodium sulphate, filtered and evaporated under vacuum to give compound 5 (50 mg, 87% yield).
$[M+1]^+$ 719

EXAMPLE 17

Preparation of Intermediate 10

A mixture of N-cyclohexylcarbodiimide and N-methylpolystyrene (1.8 g, 1.69 mmol/g) in $CH_2Cl_2$ (40 ml) was centrifuged for 5 minutes, chloroacetic acid (216 mg, 2.28 mmol) and intermediate 2 (1.5 g, 2.078 mmol) were sequentially added and the mixture was centrifuged at 300 rpm for 40 hours. The solution was filtered from the resin while washing with methanol, and the filtrate was evaporated under vacuum. Purification by chromatography on Varian Mega Bond Elut (10 g silica/60 ml cartridge), eluting with $CH_2Cl_2$ and methanol (gradient from 0% to 10%), gave intermediate 10 (1.1 g, 66% yield) as a white solid.
$[M+1]^+$ 799

EXAMPLE 18

Preparation of Intermediate 11

A solution of intermediate 10 (500 mg, 0.626 mmol), triethylamine (0.35 ml, 2.5 mmol) and dimethylaminoethyleneamine (0.082 ml, 0.75 mmol) in THF (10 ml) was refluxed for 16 hours. The reaction mixture was evaporated and purified by Biotage chromatography (40S silica cartridge, 20/1/0.1 $CH_2Cl_2$/MeOH/$NH_3$ eluent) to give intermediate 11 (400 mg, 75% yield) as a white solid.
$[M+1]^+$ 851

EXAMPLE 19

Preparation of Compound 6

Compound 6 was prepared from intermediate 11 (270 mg, 0.323 mmol) according to the procedures described for compound 1. Purification by preparative HPLC and elution through a C18 cartridge gave compound 6 (100 mg, 45% yield).
$[M+1]^+$ 693

EXAMPLE 20

Preparation of Intermediate 12

Intermediate 12 was prepared from intermediate 2 (488 mg, 0.67 mmol) and from allyl [2-(allyloxycarbonyl-2-thiazolylmethyl-amino)ethyl](2-oxoethyl)carbamate (248 mg, 0.67 mmol) according to the procedures described for intermediate 7. Purification by Biotage chromatography (40M silica cartridge, 20/1/0.1 $CH_2Cl_2$/MeOH/$NH_3$ eluent) gave intermediate 12 (390 mg, 55% yield) as a brown oil.
$[M+1]^+$ 1074

EXAMPLE 21

Preparation of Intermediate 13

Pyrrolidine (0.083 ml, 1 mmol) and tetrakis(triphenylphosphine) palladium (20 mg, 0.02 mmol) were sequentially added to a solution of intermediate 1.2 (380 mg, 0.354 mmol) in $CHCl_3$ (5 ml) maintained under an argon atmosphere. The reaction mixture was stirred for 2 hours, neutralized with water (10 ml), the organic phase was separated out and the aqueous phase was extracted with $CH_2Cl_2$ (2×10 ml). The combined organic phase was dried over sodium sulphate, filtered and evaporated under vacuum to give a crude oil. Purification by Biotage chromatography (12M silica cartridge, 15/1/0.1 $CH_2Cl_2$/MeOH/$NH_3$ eluent) gave intermediate 13 (180 mg, 56% yield).
$[M+1]^+$ 906

EXAMPLE 22

Preparation of Compound 7

Compound 7 was prepared from intermediate 13 (128 mg, 0.141 mmol) according to the procedure described for compound 1. The reaction mixture was diluted with distilled water (20 ml) and the methanol was evaporated off under vacuum to give an aqueous phase, which was washed with $CH_2Cl_2$ (3×10 ml), concentrated aqueous ammonia was added to pH>7, and the mixture was extracted with $CH_2Cl_2$ (3×10 ml). The combined organic phase was dried over sodium sulphate, filtered and evaporated under vacuum to give compound 7 (50 mg, 47% yield).
$[M+1]^+$ 748

EXAMPLE 23

Preparation of Intermediate 14

Intermediate 14 was prepared from intermediate 2 (500 mg, 0.693 mmol) and from allyl [2-(allyloxycarbonylphenyl-methylamino) ethyl](2-oxoethyl)carbamate (256 mg, 0.7 mmol), according to the procedures described for intermediate 7. Purification by Biotage chromatography (40M silica cartridge, 40/1/0.1 $CH_2Cl_2$/MeOH/$NH_3$ eluent) gave intermediate 14 (600 mg, 82% yield) as oil.
$[M+1]^+$ 1067

EXAMPLE 24

Preparation of Intermediate 15

Intermediate 15 was prepared from intermediate 14 (594 mg, 0.557 mmol) according to the procedures described for intermediate 13. Purification by Biotage chromatography (40S silica cartridge, 30/1/0.1 $CH_2Cl_2$/MeOH/$NH_3$ eluent) gave intermediate 15 (310 mg, 62% yield) as a white solid.
$[M+1]^+$ 899

EXAMPLE 25

Preparation of Compound 8

Compound 8 was prepared from intermediate 15 (250 mg, 0.278 mmol) according to the procedures described for compound 1. Purification by Biotage chromatography (12M silica cartridge, 30/1/0.1 $CH_2Cl_2$/MeOH/$NH_3$ eluent) gave compound 8 (110 mg, 54% yield) as a white solid.
$[M+1]^+$ 741

EXAMPLE 26

Preparation of Intermediate 16

$NaBH_4$ (160 mg, 4.2 mmol) was added portionwise to a solution of 3'-desdimethylamino-3',4'-dehydroerythromycin A (1.3 g, 1.9 mmol) prepared as described in J. Am. Chem. Soc., 1981, 103, (11), 3213-3215, in THF (10 ml) and methanol (20 ml). The reaction mixture was stirred overnight at room temperature, neutralized by addition of acetic acid (1 ml) and, after stirring for a further 30 minutes, concentrated $NH_3$ was added to basic pH. The solvent was evaporated off under vacuum and the crude mixture was dissolved in ethyl acetate (100 ml) and washed with 20% NaCl solution (3×100 ml). The organic phase was dried over sodium sulphate, filtered and evaporated under vacuum. Purification by Biotage chromatography (40M silica cartridge, 35/1 $CH_2Cl_2$/MeOH eluent) gave intermediate 16 (800 mg, 65% yield) as a white solid.
$[M+1]^+$ 692

EXAMPLE 27

Preparation of Compound 9

Compound 9 was prepared from intermediate 16 (600 mg, 0.868-mmol) according to the procedures described for compound 1. Purification by Biotage chromatography (40M silica cartridge, 37/1 $CH_2Cl_2$/MeOH eluent) gave compound 9 (380 mg, 82% yield) as a white solid.
$[M+1]^+$ 534

EXAMPLE 28

Preparation of Compound 10

$PtO_2$ (1-0 mg) was added in a high-pressure crucible to a solution of compound 9 (300 mg, 0.56 mmol) in absolute ethanol. After a sequence of 3 cycles of hydrogenation, the reaction mixture was maintained under a hydrogen atmosphere at 45 psi. After 4 hours, the mixture was filtered through a pad of Celite and evaporated under vacuum to give compound 10 (300 mg, 99.9% yield) as an amorphous white solid.
$[M+1]^+$ 536

EXAMPLE 29

Preparation of Compound 11

Compound 11 was, prepared from erythromycin A oxime (2.5 g, 3.34 mmol) according to the procedures described for compound 1. Purification by Biotage chromatography (40M silica cartridge, 90/5/0.5 $CH_2Cl_2$/MeOH/$NH_3$ eluent) gave compound 11 (1.8 g, 91% yield) as a white solid.
$[M+1]^+$ 592

EXAMPLE 30

Preparation of Compound 12

Compound 12 was prepared from erythromycin A oxime N-oxide (3 g, 3.83 mmol), prepared as described in international patent application WO 00/42055, Example 4, in the name of Zambon Group, according to the procedures described for compound 1. Purification by Biotage chromatography (40M silica cartridge, 90/10/1 $CH_2Cl_2$/MeOH/$NH_3$ eluent) gave compound 12 (1.5 g, 65% yield) as a white solid.
$[M+1]^+$ 608

EXAMPLE 31

Preparation of Compound 13

Compound 13 was prepared from 3'-desdimethylamino-3',4'-dehydro erythromycin A oxime (30 g, 42.6 mmol), prepared as described in international patent application WO 00/42055, Example 5, in the name of Zambon Group, according to the procedures described for compound 1. Purification by flash chromatography (silica, 90/7 $CH_2Cl_2$/MeOH eluent) gave compound 13 (19.2 g, 82% yield) as a white solid.
$[M+1]^+$ 546.

EXAMPLE 32

Preparation of Compound 14

Compound 14 was prepared from 3'-desdimethylamino-erythromycin A oxime (36.2 g, 51.3 mmol), prepared as described in international patent application WO 00/42055, Example 6, in the name of Zambon Group, according to the procedures described for compound 1. Purification by flash chromatography (silica, 97/3 to 95/5 $CH_2Cl_2$/MeOH eluent) gave compound 14 (22.1 g, 79% yield) as a white solid.
$[M+1]^+$ 548

EXAMPLE 33

Preparation of Intermediate 17

O-Methylhydroxylamine hydrochloride (10 g, 197 mmol) was added to a solution of erythromycin A 21.9 g, 29.9 mmol) in methanol (150 ml) maintained under a nitrogen atmosphere, followed, after 10 minutes, by addition of triethylamine (8.33 ml, 59.8 mmol). After stirring for one day, the reaction mixture was neutralized with aqueous 10% ammonia solution (300 ml) and the solid thus formed was filtered off, washed with water and air-dried for 3 days. Purification by flash chromatography (50/50/10 $CHCl_3$/hexane/triethylamine eluent) gave intermediate 17 (7 g, 31% yield) as a white crystalline solid.
$[M+1]^+$ 764

EXAMPLE 34

Preparation of Compound 15

Compound 15 was prepared from intermediate 17 (400 mg, 0.52 mmol) according to the procedures described for compound 1. Purification by Variant Mega bond Elut (10 g silica cartridge, from $CH_2Cl_2$ to 90/5/0.5 $CH_2Cl_2$/MeOH/$NH_3$ eluent) gave compound 15. (249 mg, 78.8% yield) as a white solid.
$[M+1]^+$ 764

EXAMPLE 35

Preparation of Intermediate 18

Intermediate 18 was prepared from intermediate 17 (0.9 g, 1.18 mmol) according to the procedures described for intermediate 5. The product (0.91 g, 99% yield) was extracted in pure form without further purification, as a pale yellow solid.
$[M+1]^+$ 779

EXAMPLE 36

Preparation of Compound 16

Compound 16 was prepared from intermediate 18 (720 mg, 0.92 mmol) according to the procedures described for compound 1. Purification by Variant Mega bond Elut (20 g silica cartridge, from $CH_2Cl_2$ to 90/10/1 $CH_2Cl_2$/MeOH/$NH_3$ eluent) gave compound 16 (430 mg, 84% yield) as a white solid.
$[M+1]^+$ 621

EXAMPLE 37

Preparation of Intermediate 19

Intermediate 19 was prepared from intermediate 18 (500 mg, 0.64 mmol) according to the procedures described for 3'-desdimethylamino-3',4'-dehydroerythromycin A oxime, prepared as described in international patent application WO 00/42055, Example 5, in the name of Zambon Group. Purification by Variant Mega bond Elut (10 g silica cartridge, from $CH_2Cl_2$ to 95/5 $CH_2Cl_2$/MeOH eluent) gave intermediate 19 (150 mg, 32% yield) as a white solid.
$[M+1]^+$ 718

EXAMPLE 38

Preparation of Compound 17

Compound 17 was prepared from intermediate 19 (720 mg, 0.92 mmol) according to the procedures described for compound 1. Purification by Variant Mega bond Elut (10 g silica cartridge, from $CH_2Cl_2$ to 100/1 $CH_2Cl_2$/MeOH eluent) gave compound 17 (130 mg, 68% yield) as a white solid.
$[M+1]^+$ 560

EXAMPLE 39

Preparation of Intermediate 20

Intermediate 20 was prepared from intermediate 19 (143 mg, 0.20 mmol) according to the procedures described for 3'-desdimethylamino erythromycin A oxime, prepared as described in international patent application WO 00/42055, Example 6, in the name of Zambon Group. After filtration through a pad of Celite and evaporation under vacuum, pure intermediate 20 (120 mg, 83.3% yield) was obtained as a white solid.
$[M+1]^+$ 720

EXAMPLE 40

Preparation of Compound 18

Compound 18 was prepared from intermediate 20 (720 mg, 0.92 mmol) according to the procedures described for compound 1. Purification by Biotage chromatography (12M silica cartridge, 100/1.5 $CH_2Cl_2$/MeOH eluent) gave compound 18 (121 mg, 66% yield) as a white solid.
$[M+1]^+$ 562

EXAMPLE 41

Preparation of 2-[2-[(2-thiazolylmethyl)amino]ethylamino]ethanol (Intermediate 21)

3 Å molecular sieves (22.5 g) and a solution of 2-thiazolecarboxaldehyde (14.5 g, 128 mmol) in ethanol (90 ml) were sequentially added to a solution of 2-(2-aminoethylamino)ethanol (13.35 g, 128 mmol) in anhydrous ethanol. The reaction mixture was stirred for 4 hours, filtered through a pad of Celite while washing with ethanol (100 ml) and placed in a high-pressure flask. After adding acetic acid (3 ml) and Pd (10% on C, 2 g), the solution was introduced into Parr apparatus and, after several hydrogenation cycles, was stirred for 2 days under a hydrogen atmosphere at 40 psi. The reaction mixture was filtered through a pad of Celite, evaporated under vacuum and purified by flash chromatography (silica, 80/20/10 $CH_2Cl_2$/MeOH/$NH_3$ eluent) to, give 2-[2-[(2-thiazolylmethyl)amino]ethylamino]ethanol (15.4 g, 60% yield) as a brown oil.
$[M+1]^+$ 202

EXAMPLE 42

Preparation of allyl[2-(allyloxycarbonyl-2-thiazolyl-methylamino)ethyl](2-hydroxyethyl)carbamate (Intermediate 22)

A solution, at 0° C., of allyl formate (1.22 ml, 11.5 mmol) in $CH_2Cl_2$ (30 ml) was added dropwise over 30 minutes to a solution of intermediate 21 (1.16 g, 5.76 mmol and $K_2CO_3$ (1.14 g, 8.4 mmol) in $CH_2Cl_2$ (30 ml) and $H_2O$ (50 ml). After stirring at room temperature for 16 hours and diluting with $K_2CO_3$ (50 ml of an aqueous 10% solution), the organic layer was separated out and the aqueous phase was extracted with $CH_2Cl_2$ (2×40 ml). The combined organic phase was washed with citric acid (50 ml of an aqueous 5% solution), dried over sodium sulphate and filtered, the solvent was evaporated off and the residue was purified by flash chromatography (silica, 18/1 $CH_2Cl_2$/MeOH eluent) to give intermediate 22 (1.27 g, 60% yield) as a brown oil.
$[M+1]^+$ 370

EXAMPLE 43

Preparation of ethyl 2-[allyloxycarbonyl[2-(allyloxycarbonyl-2-thiazolylmethylamino)ethyl]amino]methanesulphonate (Intermediate 23)

A solution, at 0° C., of mesyl chloride (3.64 ml, 47 mmol) in $CH_2Cl_2$ (10 ml) was added dropwise over 15 minutes to a solution of intermediate 22 (12.96 g, 35 mmol) and triethylamine (9.74 ml, 70 mmol) in $CH_2Cl_2$ (130 ml). After 1 hour, the starting material had reacted and the reaction mixture was diluted with $CH_2Cl_2$ (50 ml) and washed with 50 ml of 5% citric acid, 50 ml of 5% $NaHCO_3$ and a 20% NaCl solution (50 ml). The organic phase was dried over sodium sulphate and filtered, and the solvent was evaporated off under vacuum to give intermediate 23 (1.6 g, quantitative yield) as a red oil, which was used immediately in the next reaction.
$[M+1]^+$ 448

EXAMPLE 44

Preparation of Intermediate 24

A solution of potassium tert-butoxide (3.6 g, 32.1 mmol) in THF (180 ml) was prepared in an anhydrous flask maintained under a nitrogen atmosphere. 3'-Desdimethylaminoerythromycin A oxime (20.6 g, 29.2 mmol) was added to the reaction mixture and the resulting mixture was stirred for 30 minutes, followed by sequential addition of 18-crown-6 ether (7.72 g, 29.2 mmol) and, dropwise over more than 30 minutes, a solution of intermediate 23 (15.7 g, 35 mmol) in THF (70 ml). After 18 hours, the mixture was evaporated under vacuum, diluted with 20% NaCl solution (0.5 L) and extracted with ethyl acetate (3×0.5 L). The combined organic, phase was dried over sodium sulphate and filtered, the solvent was evaporated off under vacuum and the residue was purified by flash chromatography (silica, 95/5 $CH_2Cl_2$/MeOH eluent) to give intermediate 24 (20 g, 65% yield) as a white solid.
$[M+1]^+$ 1058

EXAMPLE 45

Preparation of Intermediate 25

Intermediate 25 was prepared from erythromycin A oxime (4.2 g, 9.82 mmol) according to the procedure described for intermediate 24. Purification by flash chromatography (silica, 95/5/0.5 $CH_2Cl_2$/MeOH/$NH_3$ eluent) gave intermediate 25 (8.2 g, 76% yield) as a solid.
$[M+1]^+$ 1101

EXAMPLE 46

Preparation of Intermediate 26

Intermediate 26 was prepared from intermediate 25 (1.1 g, 1 mmol) according to the procedures described for the preparation of erythromycin A oxime N-oxide (international patent application WO 00/42055, Example 4, in the name of Zambon Group). The crude reaction mixture was evaporated under vacuum (twice, after dilution with distilled water, and twice, after dilution with $CH_2Cl_2$) to give intermediate 26 (1 g, 90% yield) as a solid that was pure enough for the next synthesis step.
$[M+1]^+$ 1117

EXAMPLE 47

Preparation of Intermediate 27

Morpholine (2.3 g, 2.7 mmol), triphenylphosphine (262 mg, 1 mmol) and palladium(II) acetate (75 mg, 0.34 mmol) were sequentially added to a solution of intermediate 24 (14 g, 13.2 mmol) in $CH_2Cl_2$ (140 ml) maintained under an argon atmosphere. The reaction mixture was stirred for 2 hours and neutralized with water (50 ml), the organic phase was separated out and the aqueous phase was extracted with $CH_2Cl_2$ (2×50 ml). The combined organic phase was dried over sodium sulphate, filtered and evaporated under vacuum to give a crude oil (13.4 g). Purification by atmospheric-pressure chromatography (230/70 mesh silica, 90/9/0.9 $CH_2Cl_2$/MeOH/$NH_3$ eluent) gave intermediate 27 (9.3 g, 79% yield) as a white solid.

Intermediate 27 is a known compound described in international patent application WO 00/42055, Example 9, in the name of Zambon Group.

EXAMPLE 48

Preparation of Intermediate 28

Intermediate 28 was prepared from intermediate, 25 (1.55 g, 1.41 mmol) according to the procedures described for intermediate 27, replacing the morpholine with pyrrolidine (0.5 g, 7 mmol). Purification by atmospheric-pressure chromatography (230/70 mesh silica, 90/10/1 $CH_2Cl_2$/MeOH/$NH_3$ eluent) gave intermediate 28 (1 g, 76% yield) as a solid.
$[M+1]^+$ 933

EXAMPLE 49

Preparation of Intermediate 29

Intermediate 29 was prepared from intermediate 26 (1 g, 1.41 mmol) according to the procedures described for intermediate 27. Purification by Biotage chromatography (40M silica cartridge, 90/10/1 $CH_2Cl_2$/MeOH/$NH_3$ eluent) gave intermediate 29 (0.76 g, 90% yield) as a solid.
$[M+1]^+$ 949

EXAMPLE 50

Preparation of Compound 19

Compound 19 was prepared from intermediate 28 (600 mg, 0.64 mmol) according to the procedures described for compound 1. Given that the product is water-soluble, the crude solid was dissolved in water (50' ml) and washed with $CH_2Cl_2$ (3×20 ml). The solvent was evaporated from the aqueous phase under vacuum and dried to give compound 19 (480 mg, 95% yield) as a crystalline solid.
$[M+1]^+$ 775

EXAMPLE 51

Preparation of Compound 20

Compound 20 was prepared from intermediate 29 (450 mg, 0.47 mmol) according to the procedures described for compound 1. Purification by Biotage chromatography (40M silica cartridge, 90/10/1 $CH_2Cl_2/MeOH/NH_3$ eluent) gave compound 20 (180 mg, 49% yield) as a white solid.
$[M+1]^+$ 791

EXAMPLE 52

Preparation of Compound 21

Compound 21 was prepared from intermediate 27 (2.6 g, 2.92 mmol) according to the procedures described for compound 1. Purification by atmospheric-pressure chromatography (silica, 90/8/0.8 $CH_2Cl_{21}MeOH/NH_3$ eluent) gave compound 21 (1.84 mg, 86% yield) as a crystalline white solid.
$[M+1]^+$ 732

EXAMPLE 53

Preparation of ethyl 2-(benzylbenzyloxycarbonylamino) methanesulphonate

See international patent application WO 96/18633, Example 1, in the name of Zambon Group.

EXAMPLE 54

Preparation of Intermediate 30

Intermediate 30 was prepared from erythromycin A oxime (8.74 g, 11.7 mmol) and ethyl 2-(benzylbenzyloxycarbonylamino)methane sulphonate (4.24 g, 11.7 mmol) according to the procedure described for intermediate 24. Purification by flash chromatography (silica, 95/5/0.5 $CH_2Cl_2/MeOH/NH_3$ eluent) gave intermediate 30 (8.5 g, 72% yield).

EXAMPLE 55

Preparation of Intermediate 31

10% Pd/C (0.85 g) was added to a solution of intermediate 30 (8.5 g, 8.36 mmol) in anhydrous ethyl alcohol (180 ml) and, after 3 hydrogenation cycles, the mixture was stirred in the Parr apparatus under a hydrogen atmosphere at 20 psi. After one hour, the reaction mixture was filtered through a pad of Celite, the solvent was evaporated off and the residue was purified by flash chromatography (silica, 95/5/0.5 $CH_2Cl_2/MeOH/NH_3$ eluent) to give intermediate 31 (5 g, 67% yield) as a white solid.
$[M+1]^+$ 883

EXAMPLE 56

Preparation of Compound 22

Compound 22 was prepared from intermediate 31 (0.5 g, 0.57 mmol) according to the procedures described for compound 1. Purification by Biotage chromatography (12M silica cartridge, 80/4/0.4 $CH_2Cl_2/MeOH/NH_3$ eluent) gave compound 22 (0.36 mg, 87% yield) as a white solid.
$[M+1]^+$ 725

EXAMPLE 57

Preparation of erythromycin A (E)-9-[O-[2-[6-[(2-trifluoromethylphenyl methylamino]hexylamino] ethyl]oxime](Intermediate 32)

The preparation was performed as described in international patent application WO 96/18633, Example 19, in the name of Zambon Group.

EXAMPLE 58

Preparation of Intermediate 33

2-Thiazolecarboxaldehyde (1 g, 8.57 mmol), $NaCN(BH_3)$ (0.9 g, 13.71 mmol) and acetic acid (2 ml) were sequentially added to a solution of intermediate 32 (7.64 g, 8.57 mmol) in $CH_2Cl_2$ (60 ml). The reaction mixture was stirred for 16 hours, filtered through a pad of Celite while washing with $CH_2Cl_2$ (20 ml), and was diluted with aqueous acetic, acid solution (pH 5, 50 ml). The aqueous solution was washed with $CH_2Cl_2$ (3×30 ml), $NaHCO_3$ was added to pH 8 and the mixture was extracted with $CH_2Cl_2$ (3×30 ml). The dilute organic phase was dried over sodium sulphate, filtered and evaporated under vacuum. Purification by flash chromatography (silica, 90/10/1 $CH_2Cl_2/MeOH/NH_3$ eluent) gave intermediate 33 (2.04 g, 24% yield) as a white solid.
$[M+1]^+$ 989

EXAMPLE 59

Preparation of Compound 23

Compound 23 was prepared from intermediate 33 (100 mg, 0.1 mmol) according to the procedures described for compound 1. Purification by Biotage chromatography (12S silica cartridge, 15/1/0.1 $CH_2Cl_2/MeOH/NH_3$ eluent) gave compound 23 (50 mg, 61% yield) as a white solid.
$[M+1]^+$ 831

EXAMPLE 60

Preparation of 3'-desdimethylaminoerythromycin A (E)-9-[O-[2-[2-(benzyloxycarbonylamino)ethyl]benzyloxycarbonylamino]ethyl]oxime](Intermediate 34)

The preparation was performed as described in international patent application WO 00/42055, Example 7, in the name of Zambon Group.

EXAMPLE 61

Preparation of Intermediate 35

Molecular sieves (1.8 g) and 3-furaldehyde (98 mg, 1 mmol) were added to a solution of intermediate 34 (0.8 g, 1 mmol) in ethanol (16 ml), and the mixture was stirred for 3 hours. After filtration through a pad of Celite, $NaBH_4$ (29 mg, 0.75 mmol) was added, to the solution, and the resulting mixture was stirred for a further one hour and evaporated under vacuum. The crude material was dissolved in ethyl acetate and washed with saturated NaCl. The organic phase was dried over sodium sulphate, filtered and evaporated under vacuum. Purification by flash chromatography (silica, 90/6/0.6 $CH_2Cl_2$/MeOH/$NH_3$ eluent) gave intermediate 35 (530 mg, 60% yield) as a solid.
$[M+1]^+$ 872

EXAMPLE 62

Preparation of Intermediate 36

Intermediate 36 was, prepared from intermediate 34 (800 mg, 1 mmol) and thiophenecarboxaldehyde (115 mg, 1 mmol) according to the procedures described for intermediate 35. Purification by flash chromatography (silica, 90/6/0.6 $CH_2Cl_2$/MeOH/$NH_3$ eluent) gave intermediate 36 (362 mg, 40% yield) as a white solid.
$[M+1]^+$ 888

EXAMPLE 63

Preparation of Intermediate 37

Intermediate 37 was prepared from intermediate 34 (800 mg, 0.1 mmol) and 2-furaldehyde (98 mg, 1 mmol) according to the procedures described for intermediate 35. Purification by flash chromatography (silica, 90/6/0.6 $CH_2Cl_2$/MeOH/$NH_3$ eluent) gave intermediate 37 (475 mg, 54% yield) as a white solid.
$[M+1]^+$ 872

EXAMPLE 64

Preparation of Compound 24

Compound 24 was prepared from intermediate 35 (200 mg, 0.22 mmol) according to the procedures described for compound 1. Purification by flash chromatography (silica, 90/5/0.5 $CH_2Cl_2$/MeOH/$NH_3$ eluent) gave compound 24 (120 mg, 73% yield) as a white solid.
$[M+i]^+$ 715

EXAMPLE 65

Preparation of Compound 25

Compound 25 was prepared from intermediate 36 (200 mg, 0.22 mmol) according to the procedures described for compound 1. Purification by Biotage chromatography (12M silica, 90/5/0.5 $CH_2Cl_2$/MeOH/$NH_3$ eluent) gave compound 25 (130 mg, 81% yield) as a white solid.
$[M+1]^+$ 731

EXAMPLE 66

Preparation of Compound 26

Compound 26 was prepared from intermediate 37 (200 mg, 0.23 mmol) according to the procedures described for compound 1. Purification by Biotage chromatography (12M silica, 90/5/0.5 $CH_2Cl_2$/MeOH/$NH_3$ eluent) gave compound 26 (125 mg, 76% yield) as a white solid.
$[M+1]^+$ 715

EXAMPLE 67

Preparation of Intermediate 38

Intermediate 38 was prepared from clarythromycin (1 g, 1.33 mmol) according to the procedures described for intermediate 16. Purification by flash chromatography (silica, 90/10/1 $CH_2Cl_2$/MeOH/$NH_3$ eluent) gave intermediate 38 (500 mg, 50% yield) as a white solid.
$[M+1]^+$ 751

EXAMPLE 68

Preparation of Compound 27

Compound 27 was prepared from intermediate 38 (202 mg, 0.27 mmol) according to the procedures described for compound 1. Purification by preparative HPLC (mobile phase: water/acetonitrile from 95/5 to 60/40 over 10 minutes) gave compound 27 (55 mg, 36% yield) as a white solid.
$[M+1]^+$ 592

EXAMPLE 69

Preparation of Compound 28

Compound 28 was prepared from compound 27 (26 mg, 0.034 mmol) according to the procedures described for the preparation of erythromycin A oxime N-oxide (international patent application WO 00/42055 in the name of Zambon Group). The reaction mixture was diluted with water and the solvent was evaporated off (three times to remove the $H_2O_2$ completely), and dried to give compound 28 (26 g, 95% yield) as a white solid.
$[M+1]^+$ 609

EXAMPLE 70

Preparation of Intermediate 39

A suspension of clarithromycin (5 g, 6.7 mmol) in methanol (150 ml) was maintained under a gentle flow of $N_2$ with mechanical stirring. Sodium acetate (0.66 g, 8 mmol) and iodine (2.03 g, 8 mmol) were added and the resulting mixture was exposed to the light of a 400 watt lamp, taking care to maintain the temperature at 10-20° C. using an ice-water bath. After 6 hours, the solvent was evaporated off under reduced pressure, the crude product was taken up in ethyl acetate and aqueous 5% sodium metabisulphite, the aqueous phase was extracted and then basified by adding aqueous ammonia followed by extraction with dichloromethane. After drying the organic phase over anhydrous $Na_2SO_4$, filtering and evaporating off the solvent, a crude product (5.1 g) was obtained, which was purified by Biotage chromatography (40M silica cartridge, eluent: 100/3/0.3 and then 100/5/0.5 CH$_2$Cl$_2$/MeOH/NH$_3$) to give the intermediate 39 (3.2 g, 65% yield).
[M+1]$^+$ 734.5

EXAMPLE 71

Preparation of Intermediate 40

Intermediate 39 (2 g, 2.72 mmol) was dissolved in 1 N HCl solution (50 ml, 50 mmol) and stirred for 2 hours at room temperature. The solution was basified with concentrated NH$_3$ and then extracted with ethyl acetate (3×50 ml). The organic phase obtained was dried over anhydrous Na$_2$SO$_4$ and filtered, and the solvent was evaporated off to give the intermediate 40 (1.56 g, 90% yield).
[M+1]$^+$ 576.3

EXAMPLE 72

Preparation of Intermediate 41

A solution of acetic anhydride (0.168 ml, 1.78 mmol) in dioxane (3 ml) was added dropwise to a solution of intermediate 40 (0.93 g, 1.62 mmol) in dioxane (30 ml) and H$_2$O (4 ml), and the resulting mixture was stirred for 8 hours. The reaction was worked up by adding methanol and evaporating off the solvent under reduced pressure. The crude product thus obtained was diluted with 2 N HCl (50 ml) and extracted with ethyl acetate (3×50 ml). The organic solution thus obtained was dried over anhydrous Na$_2$SO$_4$ and filtered, and the solvent was evaporated off to give the intermediate 41 (0.85 g, 85% yield).
[M−1]$^−$ 616.8

EXAMPLE 73

Preparation of Compound 29

A solution of intermediate 41 (500 mg, 0.79 mmol) in ethanol (20 ml) was treated with an excess of hydroxylamine hydrochloride (1.5 g, 21.6 mmol) and triethylamine (1.5 ml, 22 mmol) and the reaction was maintained at reflux with continuous monitoring to check for the possible, decomposition of the product. After 6 hours, the solvent was evaporated from the solution and the residue was diluted in ethyl acetate and washed with saturated NaCl. The resulting organic solution was dried over anhydrous Na$_2$SO$_4$ and filtered, and the solvent was evaporated off to give a crude solid. Purification by Biotage chromatography (12M cartridge column, eluent: 100/0 and then 30/1 CH$_2$Cl$_2$/MeOH) gave the compound 29 (198 mg, 40% yield).
[M+1]$^+$ 633.4

EXAMPLE 74

Preparation of Intermediate 42

A solution of pyridinemethanol (0.5 g, 4.7 mmol) in DMF (20 ml) was placed in a suitably dried two-necked round-bottomed flask maintained, under an argon atmosphere, followed by addition of sodium hydride (60%, 0.4 g, 10 mmol). A heterogeneous solution was obtained, which was stirred for 15 minutes. A solution of 2-(2-bromoethyl)-1,3-dioxane (0.92 g, 4.7 mmol) in DMF (3 ml) was then added dropwise and the resulting mixture was left to react for 16 hours at 60° C. The reaction medium was diluted with ethyl acetate (100 ml) and washed with aqueous 10% Na$_2$CO$_3$ (3×50 ml). The organic phase was dried over anhydrous Na$_2$SO$_4$ and filtered, and the solvent was evaporated off to give a crude reaction product (1 g), which was purified by chromatography (Varian Mega Bond Elut Silica column; eluent: from 100% CH$_2$Cl$_2$ to 25/1 CH$_2$Cl$_2$/MeOH) to give the intermediate 42 (650 mg, 31% yield) as a colourless liquid.
[M+1]$^+$ 633.4
R$_t$=1.4 min
$^1$H NMR (CDCl$_3$): 8.59, 8.53, 8.01 and 7.25 (4m, 4H, Py); 4.70 (t, 1H, C—CH[—O]$_2$); 4.52 (s, 2H, CH$_2$Py); 4.09 (m, 2H, O—CH$_2$C); 3.79 (m, 2H, C—CH$_2$—C); 3.60 (m, 2H, CH$_2$ dioxane); 2.05, 1.92 and 1.3 (3m, 4H, dioxane).

EXAMPLE 75

Preparation of Intermediate 43

An excess of trifluoroacetic acid (2 ml) was added to the solution of intermediate 42 (150 mg, 0.67 mmol) in CHCl$_3$ (4 ml), and the resulting mixture was left to react at room temperature for 48 hours. The reaction medium was diluted with CH$_2$Cl$_2$ (50 ml) and washed with aqueous 10% Na$_2$CO$_3$ (3×20 ml). The organic phase was dried over anhydrous Na$_2$SO$_4$' and filtered, and the solvent was evaporated off. Purification by Biotage chromatography (12M cartridge column, eluent: 30/1/0.1 CH$_2$Cl$_2$/MeOH/NH$_3$) gave the intermediate 43 (45 mg, 40% yield), which was used directly for the following reaction.
[M+1]$^+$ 166.4
Rt=2.5 min HPLC/MS analyses were performed with a Gilson machine equipped with a C18 Zorbax SBC18 column (3.5 μm, 2.1×50 mm) and using as detector a UV diode array (220 nm), a Finnigan Aqa mass spectrometer (electron spray, positive or negative ionization) and an ELSD developer.

Conditions:

Flow rate: 1 ml/minute

Column temperature: 40° C.

A/B elution gradient (eluent A: 0.5% formic acid in water; eluent B: 0.5% formic acid in acetonitrile): t=0 min, A/B=95:5, t=8 min, A/B=5:95.

EXAMPLE 76

Preparation of Compound 30

Molecular sieves (4 Å, 100 mg), acetic acid (16 μl, 0.267 mmol) and then tert-butylaluminium hydride (120 mg, 0.445 mmol) were added to a solution of intermediates 4 (100 mg, 0.178 mmol) and 43 (30 mg, 0.178 mmol) in dichloroethane (10 ml). The mixture was left to react for 48 hours at room temperature and was then filtered through Celite and the filtrate was diluted with 10% Na$_2$CO$_3$ (20 ml) and extracted with CH$_2$Cl$_2$ (3×20 ml). The combined organic extracts were dried over anhydrous Na$_2$SO$_4$ and filtered, and the solvent was evaporated off under reduced pressure. Purification by Biotage chromatography (12M cartridge column, eluent: 30/1/0.1 CH$_2$Cl$_2$/MeOH/NH$_3$) gave the compound 30 (50 mg, 39% yield).
[M−1]$^−$ 714.5

EXAMPLE 77

In Vivo Pharmacological Activity

A) Acute Contact Dermatitis
  Animals
  Groups of 5-6 CD1 mice (18-24 g) were used.
  Administration of the compounds
  All the macrolide compounds were dissolved in Transphase Delivery System (TPDS), a vehicle formed by 10% benzyl alcohol, 40% acetone and 50% isopropanol.
  15 microlitres of the compounds (500 µg), dissolved in TPDS, were applied topically to the inner surface of an ear; 30 minutes later, 12 microlitres of a solution of tetradecanoylphorbol acetate (TPA) at a concentration of 0.01% dissolved in acetone were applied to the same area.
  Six hours later, the animals were sacrificed by inhalation of $CO_2$.
  Evaluation of the results
  Two methods were used to evaluate the auricular oedema:
  a) Weight of a given portion of auricular pinna.
  b) Measurement of the auricular thickness using precision spring callipers.
  The degree of oedema was calculated by subtracting the weight or the thickness of the untreated ear from that of the contralateral treated ear. To determine the degree of remission of the oedema, the difference (weight or thickness) of the groups treated with TPA+macrolides was then compared with the groups treated with TPA alone.
  The activity of the macrolide compounds was measured by using the modified method of Zunic et al. (1998): MDL (Lysyl) GDP, a non-toxic muramyl dipeptide derivative inhibits cytokine production by activated macrophages and protects mice from phorbol ester- and oxazolone-induced inflammation (J. Invest. Dermatol., 111(1), 77-82).
  The data relating to erythromycin and azythromycin concern the treatment with a single dose of 500 µg/ear.
  Results obtained for a number of compounds of formula I, representative of the whole class, are given in the following table.

| Compound | Oedema (% inhibition) | Method for measuring oedema |
|---|---|---|
| Erythromycin | 42 | a |
| Azythromycin | 40 | a |
| 15 | 31.6 | a |
| 16 | 72.3 | a |
| 17 | 41.9 | a |
| 18 | 54.3 | a |
| 13 | 77.4 | a |
| 14 | 71.5 | a |
| 11 | 70.2 | a |
| 12 | 87.4 | a |
| 19 | 28.2 | b |
| 20 | 49.9 | b |
| 21 | 74.1 | b |
| 3 | 65.2 | a |
| 1 | 65.6 | a |
| 2 | 36.2 | a |
| 6 | 30.9 | a |
| 5 | 53.4 | a |
| 7 | 45.0 | a |
| 9 | 32.4 | a |
| 29 | 44.5 | a |
| 30 | 39.8 | a |

B) LPS-Induced Pulmonary Inflammation in Rats
  Administration
  The rats received endotracheally, via the peroral route, a single dose of 0.4 mg/kg of LPS (*E. coli*, serotype 026:6). The tracheal instillation was performed under anaesthesia with halothane and, 20 hours after the endotracheal administration of LPS/saline solution, the animals were sacrificed by means of an overdose of urethane.
  Washing
  The lungs were washed with 4 aliquots of 5 ml each of saline solution with 10 IU $ml^{-1}$ heparin. The cell suspension was concentrated by low-speed centrifugation and the cell pellet was suspended.
  Counting of the Cells and Differentiation.
  The total cell count was performed in a haemocytometer.
  The differential counting was performed on cytospin preparations stained with May-Grunwald-Giemsa (Tamaoki J., Tagaya E., Yamawaki I., Sakai, Nagai A., Konno K, 1995. Effect of erythromycin on endotoxin-induced microvascular leakage in the rat trachea and lungs. Am. J. Respir. Crit. Care Med., 151, 1582-8). The rats received the test compounds orally in doses of 100, 40 and 10 µmol/kg as a single administration dose orally one hour before exposure to LPS.
  $ED_{50}$ value is the dose that induced a 50% reduction in the neutrophil count in the bronchial fluid wash.
  The data relating to erythromycin refers to an oral treatment with a single dose of 130 µmol/kg.
  The results obtained for a number of compounds of formula I representative of the entire class are given in the following table.

| Compound | $ED_{50}$ µmol/kg |
|---|---|
| Erythromycin | Not active |
| 14 | 15 |
| 1 | 7 |

EXAMPLE 78

In Vitro Pharmacological Activity

Antibiotic Activity
  Preparation of the test
  All the compounds were dissolved in DMSO as a 100 X concentrated solution at a concentration of 12.8 mg/ml. The concentrated solution was diluted to 1:100 in the incubation medium to a final concentration of 128 µg/ml (1% DMSO final concentration). To evaluate the MIC, successive 1:2 dilutions of the 100 X concentrated solution were prepared in DMSO and diluted to 1:100 in the incubation medium.
  Experimental method
  The MIC (minimum inhibitory concentration) or the antibiotic activity of the compounds was evaluated at 128 µg/ml.
  The MIC values were determined in liquid earth according to the method described in "Manual of Clinical Microbiology, $7^{th}$ edition (1999), American Society for Microbiology".
  The bacterial strains used are:
  *Streptococcus pneumoniae* ATCC 49619
  *Staphylococcus aureus* ATCC 29213 o ATCC 6538
  *Enterococcus faecalis* ATCC 29212
  *Streptococcus pyogenes* ATCC 19615
  Evaluation of the data The results are expressed as the MIC (μg/ml), evaluated as the lowest concentration of the test substance that fully inhibits growth visible to the naked eye.

The results obtained for a number of compounds of formula I representative of the entire class are given in the following table.

| Compounds | Staph. aureus ATCC 29213 MIC (μg/ml) | Strep. pneum ATTC 49619 MIC (μg/ml) | Enter. faecalis ATCC 29212 MIC (μg/ml) |
|---|---|---|---|
| Erythromycin | 0.25 | 0.12 | 1 |
| 23 | >128 | 8 | 64 |
| 27 | >128 | >128 | >128 |
| 19 | >128 | 16 | >128 |
| 20 | >128 | >128 | >128 |
| 21 | >128 | >128 | >128 |
| 13 | >128 | >128 | >128 |
| 3 | >128 | >128 | >128 |
| 18 | >128 | >128 | >128 |
| 1 | >128 | >128 | >128 |
| 11 | >128 | >128 | >128 |
| 12 | >128 | >128 | >128 |
| 2 | >128 | >128 | >128 |

| Compounds | Staph. aureus ATCC 6538 128 (μg/ml) | Strep. pyogenes ATTC 19615 128 (μg/ml) | Enter. faecalis ATCC 29212 128 (μg/ml) |
|---|---|---|---|
| Erythromycin | 0.25 μg/ml MIC | 0.12 μg/ml (MIC) | 1 μg/ml (MIC) |
| 15 | not active | not active | not active |
| 26 | not active | not active | not active |
| 21 | not active | not active | not active |
| 13 | not active | not active | not active |
| 3 | not active | not active | not active |
| 18 | not active | not active | not active |
| 1 | not active | not active | not active |
| 11 | not active | not active | not active |
| 12 | not active | not active | not active |
| 2 | not active | not active | not active |

The data given in the table clearly show that the compounds of formula I of the present invention are substantially free of antibiotic activity.

The invention claimed is:

1. A compound of formula

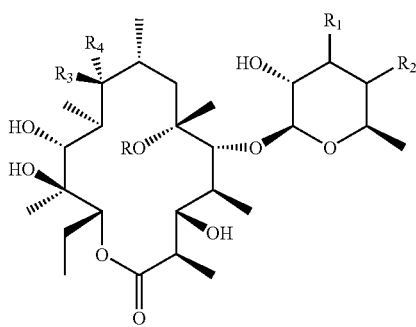

(I)

wherein

R is a hydrogen atom or a methyl group;

$R_1$ is a hydrogen atom, an N,N-dimethylamino-N-oxide group, an N-benzyl-N-methylamino group, an N-acetyl-N-methylamino group, an N-[N,N-dimethylamino($C_1$-$C_2$)alkylamino]acetyl-N-methylamino group or a chain of formula

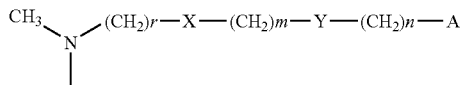

wherein

A is a hydrogen atom, a phenyl or a five- or six-membered heteroaryl ring selected from pyrrole, thiophene, furan, imidazole, oxazole, thiazole, pyridine, pyrimidine, triazole and thiadiazole;

X is O or $NR_6$ and $R_6$ is a hydrogen atom;

Y is, when n is 0, a $C_6H_4$ group or a five- or six-membered heteroaryl ring selected from pyrrole, thiophene, furan, imidazole, oxazole, thiazole, pyridine, pyrimidine, triazole and thiadiazole; or, when n is 1, $NR_6$ and $R_6$ is a hydrogen atom;

r is an integer from 1 to 3;

m is the integer 1 or 2;

n is the integer 0 or 1;

or $R_1$ forms a bond together with $R_2$;

$R_2$ is a hydrogen atom or forms a bond together with $R_1$;

$R_3$ is a hydroxy group or forms a group =N—O—$R_5$ together with $R_4$, and $R_5$ is a hydrogen atom, a linear or branched $C_1$-$C_5$ alkyl, a benzyl optionally substituted with one or two substituents selected from nitro, hydroxy, carboxy, amino, linear or branched $C_1$-$C_5$ alkyl, $C_1$-$C_4$ alkoxycarbonyl groups, aminocarbonyl groups or cyano groups or a chain of formula

wherein r, m, n, X, Y and A have the meanings given above;

$R_4$ is a hydrogen atom or forms a group =N—O—$R_5$ together with $R_3$, and $R_5$ has the meanings given above;

and the pharmaceutically acceptable salts thereof.

2. A compound according to claim 1, wherein the oxime group that may be present in position 9 is of E configuration.

3. A compound according to claim 1, wherein $R_1$ is a hydrogen atom, an N,N-dimethylamino-N-oxide group, an N-benzyl-N-methylamino group, an N-acetyl-N-methylamino group, an N-[N,N-dimethylaminoethylamino]acetyl-N-methylamino group or a chain of formula

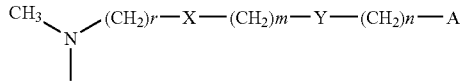

wherein

A is a hydrogen atom, a phenyl or a heteroaryl ring selected from thiophene, furan, thiazole, pyridine and triazole;

X is $NR_6$ and $R_6$ is a hydrogen atom;

Y is, when n is 0, a $C_6H_4$ group or a heteroaryl ring selected from thiophene, furan, thiazole, pyridine and triazole; or, when n is 1, $NR_6$ and $R_6$ is a hydrogen atom;

or $R_1$ forms a bond together with $R_2$.

4. A compound of formula (I):

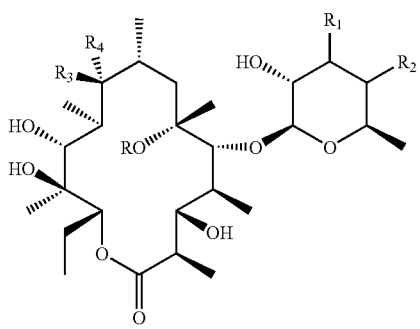
(I)

wherein

R is a hydrogen atom or a methyl group;

$R_1$ is a hydrogen atom, an N,N-dimethylamino-N-oxide group, an N-benzyl-N-methylamino group, an N-acetyl-N-methylamino group, an N-[N,N-dimethylamino($C_1$-$C_2$) alkylamino]acetyl-N-methylamino group or a chain of formula

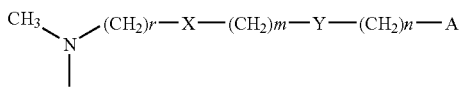

wherein

A is a hydrogen atom, a phenyl or a five- or six-membered heteroaryl ring selected from pyrrole, thiophene, furan, imidazole, oxazole, thiazole, pyridine, pyrimidine, triazole and thiadiazole;

X is O or $NR_6$ and $R_6$ is a hydrogen atom;

Y is, when n is 0, a $C_6H_4$ group or a five- or six-membered heteroaryl ring selected from pyrrole, thiophene, furan, imidazole, oxazole, thiazole, pyridine, pyrimidine, triazole and thiadiazole; or, when n is 1, $NR_6$ and $R_6$ is a hydrogen atom;

r is an integer from 1 to 3;

m is the integer 1 or 2;

n is the integer 0 or 1;

or $R_1$ forms a bond together with $R_2$;

$R_2$ is a hydrogen atom or forms a bond together with $R_1$;

$R_3$ is a hydroxy group;

$R_4$ is a hydrogen atom;

and the pharmaceutically acceptable salts thereof.

5. A compound according to claim 4, wherein $R_1$ is a hydrogen atom, an N,N-dimethylamino-N-oxide group, an N-benzyl-N-methylamino group, an N-acetyl-N-methyl amino group, an N-[N,N-dimethylaminoethylamino]acetyl-N-methylamino group or a chain of formula

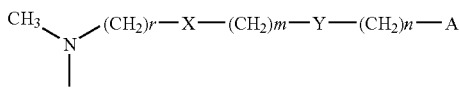

wherein

A is a hydrogen atom, a phenyl or a heteroaryl ring selected from thiophene, furan, thiazole, pyridine and triazole;

X is $NR_6$ and $R_6$ is a hydrogen atom;

Y is, when n is 0, a $C_6H_4$ group or a heteroaryl ring selected from thiophene, furan, thiazole, pyridine and triazole; or, when n is 1, $NR_6$ and $R_6$ is a hydrogen atom;

or $R_1$ forms a bond together with $R_2$.

6. A process for preparing a compound according to claim 1, characterized in that the L-cladinose moiety in 3 position is removed from the erythromycin A compounds of formula

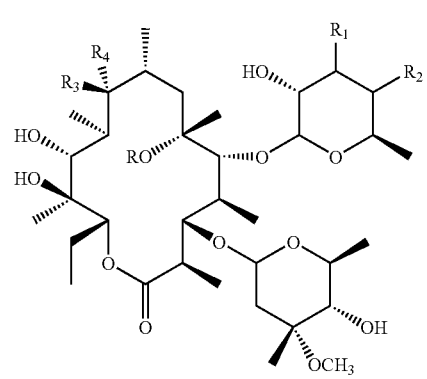
(II)

wherein R, $R_1$, $R_2$, $R_3$ and $R_4$ are defined as in claim 1;

via a hydrolysis reaction.

7. Process according to claim 6, wherein in formula II $R_3$ is a hydroxyl group and $R_4$ is a hydrogen atom.

8. Process according to claim 6, wherein the removal of the cladinose is performed via an acid hydrolysis reaction catalyzed in the presence of a mineral acid and a protic organic solvent.

9. A compound of formula II:

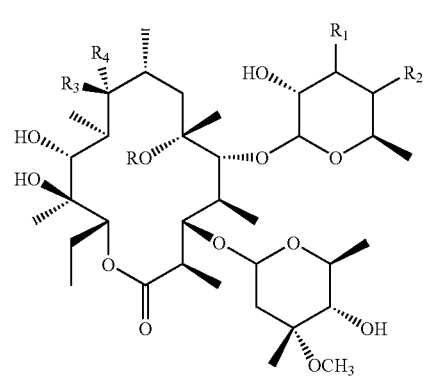
(II)

wherein

R is a hydrogen atom or a methyl group;

$R_1$ is a hydrogen atom, an N,N-di($C_1$-$C_3$)alkylamino group, an N,N-di($C_1$-$C_3$)alkylamino-N-oxide group, an N—($C_1$-$C_3$)alkyl-N-benzylamino group, an N—($C_1$-$C_4$)acyl-N—($C_1$-$C_3$)alkylamino group, an N—[N,N-dimethylamino($C_1$-$C_4$)alkylamino]acetyl-N—($C_1$-$C_3$) alkylamino group or a chain of formula

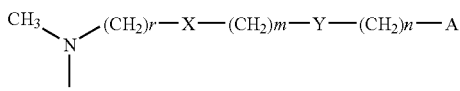

wherein
- A is a hydrogen atom, a phenyl or a five- or six-membered heteroaryl ring having from one to three hetero atoms selected from nitrogen, oxygen and sulphur;
- X is O, S, SO, $SO_2$ or $NR_6$, where $R_6$ is a hydrogen atom, a linear or branched $C_1$-$C_3$ alkyl, a $C_1$-$C_3$ alkoxycarbonyl group or a benzyloxycarbonyl group;
- Y is a $C_6H_4$ group, a five- or six-membered heteroaryl ring having from one to three hetero atoms selected from nitrogen, oxygen and sulphur or is O, S, SO, $SO_2$ or $NR_6$ where $R_6$ has the meanings given above;
- r is an integer from 1 to 3;
- m is an integer from 1 to 6;
- n is an integer from 0 to 2;
- or $R_1$ forms a bond together with $R_2$;
- $R_2$ is a hydrogen atom or forms a bond together with $R_1$;
- $R_3$ is a hydroxy group;
- $R_4$ is a hydrogen atom;
- and the pharmaceutically acceptable salts thereof;
- provided, however, that (i) $R_1$ is not an N,N-dimethyl amino group, and (ii) $R_1$ is not an N,N-dimethyl amino-N-oxide group when R is a hydrogen atom,
- and provided that one of the following limitations is met:
  - R is a hydrogen atom and $R_1$ forms a bond together with $R_2$;
  - R is a hydrogen atom and $R_1$ is an N-benzyl-N-methylamino group;
  - R is a hydrogen atom and $R_1$ is an N-acetyl-N-methylamino group;
  - R is a hydrogen atom and $R_1$ is an N—[N,N-dimethylaminoethvlamino]acetyl-N-methyl amino group;
  - R is a hydrogen atom and $R_1$ is an N-methyl-N-3-[(2-thiazolylmethyl)amino]propylamino group;
  - R is a hydrogen atom and $R_1$ is an N-2-[2-[(2-thiazolylmethyl)amino]ethylamino]ethyl-N-methylamino group; and
  - R is a hydrogen atom and $R_1$ is an N-2-[2-(benzylamino) ethylamino]ethyl-N-methylamino group.

10. A compound according to claim 9, wherein R is a hydrogen atom and $R_1$ forms a bond together with $R_2$.

11. A compound according to claim 9, wherein R is a hydrogen atom and $R_1$ is an N-benzyl-N-methylamino group.

12. A compound according to claim 9, wherein R is a hydrogen atom and $R_1$ is an N-acetyl-N-methylamino group.

13. A compound according to claim 9, wherein R is a hydrogen atom and $R_1$ is an N-[N,N-dimethylaminoethylamino]acetyl-N-methyl amino group.

14. A compound according to claim 9, wherein R is a hydrogen atom and $R_1$ is an N-methyl-N-3-[(2-thiazolylmethyl)amino]propylamino group.

15. A compound according to claim 9, wherein R is a hydrogen atom and $R_1$ is an N-2-[2-[(2-thiazolylmethyl)amino]ethylamino]ethyl-N-methylamino group.

16. A compound according to claim 9, wherein R is a hydrogen atom and $R_1$ is an N-2-[2-(benzylamino)ethylamino]ethyl-N-methylamino group.

17. The compound de(N-methyl)-9-dihydroerythromycin A.

18. The compound de(N-methyl)-descladinosyl-9-dihydro-erythromycin A.

19. A process for preparing a compound according to claim 4, wherein the L-cladinose moiety in 3 position is removed from the erythromycin A compounds of formula

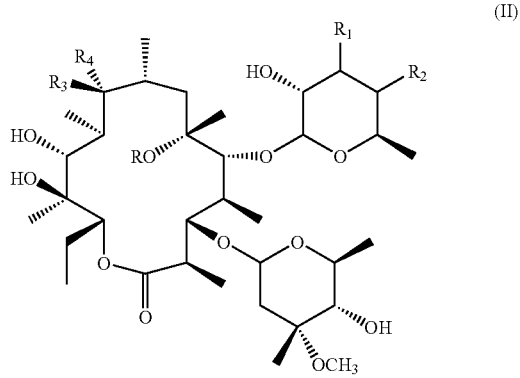

(II)

wherein R, $R_1$, $R_2$, $R_3$ and $R_4$ are defined as in claim 4;
via a hydrolysis reaction.

20. Process according to claim 19, wherein the removal of the cladinose is performed via an acid hydrolysis reaction catalyzed in the presence of a mineral acid and a protic organic solvent.

* * * * *

UNITED STATES PATENT AND TRADEMARK OFFICE
CERTIFICATE OF CORRECTION

PATENT NO.        : 7,488,811 B2
APPLICATION NO.   : 10/522671
DATED             : February 10, 2009
INVENTOR(S)       : Mauro Napoletano et al.

It is certified that error appears in the above-identified patent and that said Letters Patent is hereby corrected as shown below:

On the title page, Item (73), the Assignee information is incorrect. Item (73) should read:

-- (73) Assignee: Zambon S.p.A., Bresso, (IT) --

Signed and Sealed this

Twenty-fourth Day of November, 2009

David J. Kappos
*Director of the United States Patent and Trademark Office*